US011000562B2

(12) United States Patent
Hazan et al.

(10) Patent No.: US 11,000,562 B2
(45) Date of Patent: *May 11, 2021

(54) USE OF ISOLATED FRACTIONS OF MASTIC GUM FOR TREATING OPTIC NEUROPATHY

(71) Applicant: REGENERA PHARMA LTD., Ness Ziona (IL)

(72) Inventors: Zadik Hazan, Zikron Yaakov (IL); Konstantin Adamsky, Gedera (IL); Andre C. B. Lucassen, Rehovot (IL)

(73) Assignee: REGENERA PHARMA LTD., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/556,504

(22) PCT Filed: Mar. 7, 2016

(86) PCT No.: PCT/IL2016/050253
§ 371 (c)(1),
(2) Date: Sep. 7, 2017

(87) PCT Pub. No.: WO2016/142936
PCT Pub. Date: Sep. 15, 2016

(65) Prior Publication Data
US 2018/0071351 A1    Mar. 15, 2018

(30) Foreign Application Priority Data

Mar. 8, 2015  (IL) .......................................... 237621

(51) Int. Cl.
*A61K 36/22* (2006.01)
*A61K 47/06* (2006.01)
*A61K 47/10* (2017.01)

(52) U.S. Cl.
CPC .............. *A61K 36/22* (2013.01); *A61K 47/06* (2013.01); *A61K 47/10* (2013.01); *A61K 2236/00* (2013.01)

(58) Field of Classification Search
CPC ..................................................... A61K 36/22
See application file for complete search history.

(56) References Cited

U.S. PATENT DOCUMENTS

| 7,048,943 | B2 | 5/2006 | Barenholz |
| 2005/0238740 | A1 | 10/2005 | Fotinos |
| 2012/0003175 | A1* | 1/2012 | Hazan ..................... A61K 36/22 |
| | | | 424/78.08 |

FOREIGN PATENT DOCUMENTS

| CN | 103656290 | 3/2014 |
| EP | 1520585 | 4/2005 |
| WO | 2005112967 | 12/2005 |
| WO | 2010100650 | 9/2010 |
| WO | 2010100651 | 9/2010 |
| WO | 2013186766 | 12/2013 |

OTHER PUBLICATIONS

Aalami-Harandi (Iranian Journal of Ophthalmology, vol. 20, No. 3, 2008).*
Allcutt et al., "A qualitative comparison of the reactions of retinal ganglion cell axons to optic nerve crush in neonatal and adult mice", Developmental Brain Research, (1984) 16(2): 231-240.
Allcutt et al., "A quantitative comparison of the reactions of retinal ganglion cells to optic nerve crush in neonatal and adult mice", Developmental Brain Research, 16(1984): 219-230.
Al-Habbal et al., (1984) A Double-Blind Controlled Clinical Trial of Mastic and Placebo in the Treatment of Duodenal Ulcer. Clinical and experimental pharmacology and physiology, 11(5), 541-544.
Allcutt et al., (1984) A qualitative comparison of the reactions of retinal ganglion cell axons to optic nerve crush in neonatal and adult mice. Developmental Brain Research, 16(2), 219-230.
Al-Said et al., (1986) Evaluation of mastic, a crude drug obtained from Pistacia lentiscus for gastric and duodenal antiulcer activity. Journal of ethnopharmacology, 15(3), 271-278.
Bagnis et al., (2011) Current and emerging medical therapies in the treatment of glaucoma. Expert opinion on emerging drugs, 16(2), 293-307.
Chang & Goldberg, (2012) Glaucoma 2.0: neuroprotection, neuroregeneration, neuroenhancement. Ophthalmology, 119(5), 979-986.
Cioffi et al., (1995) An in vivo model of chronic optic nerve ischemia: The dose-dependent effects of endothelin-I on the optic nerve microvasculature. Current eye research, 14(12), 1147-1153.
Johnson & Tomarev, (2010) Rodent models of glaucoma. Brain research bulletin, 81(2), 349-358.
Kaushik et al., (2003) Neuroprotection in glaucoma. Journal of postgraduate medicine, 49(1), 90-95.
Kawasaki et al., (2002) Protective effect of arachidonic acid on glutamate neurotoxicity in rat retinal ganglion cells. Investigative ophthalmology & visual science, 43(6), 1835-1842.

(Continued)

*Primary Examiner* — Devang K Thakor

(74) *Attorney, Agent, or Firm* — Rothwell, Figg, Ernst & Manbeck, P.C.

(57) ABSTRACT

The invention relates to therapeutic uses of isolated fractions of mastic gum for treating optic neuropathy. More particularly, the invention relates to methods of treating optic neuropathy conditions using compositions comprising isolated fractions of mastic gum.

13 Claims, 3 Drawing Sheets

(56) References Cited

OTHER PUBLICATIONS

Krupin et al., (1996) an endothelin-1-induced model of chronic optic nerve ischemia in rhesus monkeys. Journal of glaucoma, 5(2), 135-138.
Otori, (2008) Use of purified retinal ganglion cells for an in vitro model to study glaucoma. Mechanisms of the Glaucomas, 601-607.
Paraschos et al., (2007) In vitro and in vivo activities of Chios mastic gum extracts and constituents against Helicobacter pylori. Antimicrobial agents and chemotherapy, 51(2), 551-559.
Sappington et al., (2010) The microbead occlusion model: a paradigm for induced ocular hypertension in rats and mice. Investigative ophthalmology & visual science, 51(1), 207-216.
Morimoto (2013) A new strategy for the treatment of various intractable optic nerve diseases. Neuro-Ophthalmology Japan 30(1): 43-52. Abstract.

\* cited by examiner

USE OF ISOLATED FRACTIONS OF MASTIC GUM FOR TREATING OPTIC NEUROPATHY

CROSS-REFERENCE TO RELATED APPLICATIONS

The present application is a national stage filing under 35 U.S.C. § 371 of PCT/IL2016/050253, filed on Mar. 7, 2016, which claims priority under 35 U.S.C. § 119 to Israeli Patent Application No. 237621, filed on Mar. 8, 2015. Each application is incorporated herein by reference in its entirety.

FIELD OF THE INVENTION

The invention relates to therapeutic uses of isolated fractions of mastic gum for treating optic neuropathy, such as optical nerve ischemia and glaucoma. More particularly, the invention relates to methods of treating such optic neuropathy conditions using compositions comprising isolated fractions of mastic gum.

BACKGROUND OF THE INVENTION

Mastic, also known as gum mastic or mastic gum, is a tree resin obtained as an exudate from *Pistacia lentiscus* L., a member of the family Anacardiaceae. Mastic was used in the ancient Mediterranean world for treating various conditions, such as, gastrointestinal disorders such as gastralgia, dyspepsia and peptic ulcer. Oral administration of mastic to human patients with duodenal ulcer and to experimental rats with induced gastric and duodenal ulcers has been disclosed to have therapeutic effects (Al-Habbal et al (1984) Clin Exp Pharmacop Physio 11(5):541-4; Said et al (1986) J Ethnopharmacol 15(3):271-8).

U.S. Patent Application Publication No 2005/0238740 discloses that certain fractions extracted from mastic resin exhibit anti-microbial and anti-cell proliferative activities.

Paraschos et al (2007), authored by some of the inventors of the aforementioned patent application, disclose preparation of a total mastic extract without polymer (TMEWP), prepared by polar solvent extraction of crude mastic and removal of the insoluble polymer poly-β-myrcene therefrom, and acidic and neutral fractions separated from TMEWP (Paraschos et al (2007) Antimicrob Agents Chemother 51(2):551-559).

EP Patent Application No. 1520585 discloses use of a product obtained from a plant of the genus *Pistacia* for the manufacture of a medicament for treating or preventing cancer.

International Patent Application Publication No. WO 2005/112967 discloses the purification from mastic of anti-cancer material having anti-proliferative effects, which is found in a soluble fraction obtained by suspending mastic in a solvent selected from a non-acidic, aliphatic hydrocarbon, an aqueous solution containing at least 25% of a water-soluble, non-acidic, aliphatic hydrocarbon, or a combination thereof, and removing the insoluble fraction.

International Patent Application Publication No. WO 2013/186766 to some of the inventors of the present application, relates to compositions and formulations comprising isolated fractions derived from Cupressaceae plant material, use thereof for treating fibrotic conditions and neurodegenerative disorders.

International patent application publication No. WO 2010/100650 to some of the inventors of the present application, relates to therapeutic uses of gum mastic, and compounds found therein including polymeric myrcene, and to methods of treating impaired neurological function using compositions comprising polymeric myrcene.

International patent application publication No. WO 2010/100651 to some of the inventors of the present application, relates to compositions isolated from mastic gum, and their therapeutic use and to compositions comprising an isolated fraction of polymeric myrcene and formulations which maintain the biological activity of the active polymer.

Chinese Patent No. CN 103656290 discloses a method for the treatment and preparation of optic atrophy, which is mainly composed of a combination of compounds, including, rehmannia, cicada, *angelica, astragalus*, Breit, frankincense, myrrh, mulberry, Scrophulariaceae and other drugs prepared by a certain weight ratio. A drug of the disclosure has Shugan eyesight, detoxification, cooling Run liver function, for the treatment of optic atrophy quickly, effectively, with non-toxic side effects.

The optic nerve contains axons of nerve cells that emerge from the retina, leave the eye at the optic disc, and go to the visual cortex where input from the eye is processed into vision. Optic neuropathy refers to damage to the optic nerve due to any cause. Damage and death of these nerve cells, leads to characteristic features of optic neuropathy. The main symptom is loss of vision, with colors appearing subtly washed out in the affected eye. On medical examination, the optic nerve head can be visualized by an ophthalmoscope. A pale disc is characteristic of long-standing optic neuropathy. In many cases, only one eye is affected and patients may not be aware of the loss of color vision until physical inspection.

Optic neuropathy can result from various reasons, such as, Ischemic optic neuropathy, Optic neuritis, Compressive optic neuropathy, Infiltrative optic neuropathy, Traumatic optic neuropathy, mitochondrial optic neuropathy, Nutritional optic neuropathies, toxic optic neuropathies, hereditary optic neuropathies, and the like. Very few treatments of optical neuropathy are currently used, and most have a limited effect on specific type of optic neuropathy.

Glaucoma is one of the leading cause of blindness in the world. There are a variety of different types of glaucoma, all sharing the same pathophysiology of retinal ganglion cells (RGCs) loss (Neuroprotection in glaucoma, Kaushik S, Pandav S S, Ram J J Postgrad Med. 2003 January-March; 49(1):90-5). The most common forms of glaucoma are primary open angel glaucoma (POAG), Primary close glaucoma (PCAG), primary congenital glaucoma (PCG). Glaucoma can also arise as a secondary complication of other pathophysiological conditions. Examples for secondary glaucomas are pigmentary, steroid-induced, exfoliation, angle recession, phacolitic and vascular glaucoma. The common mechanism of the disease is the elevated intraocular pressure (TOP) that induces stress on the RGCs and consequentially leads to their gradual loss. Therapeutic approaches that delay or halt RGCs loss have been recognized to be potentially beneficial to preserve vision in glaucoma. Indeed, currently available treatments focus on intraocular pressure (TOP) reduction, either by drugs or surgical intervention (Current and emerging medical therapies in the treatment of glaucoma, Bagnis A, Papadia M, Scotto R, Traverso C E, Expert Opin Emerg Drugs. 2011 June; 16(2):293-307). Additionnally, neuroregenerative therapies might have the potential to halt RGC loss through cell survival mechanisms (Glaucoma 2.0: neuroprotection, neuroregeneration, neuroenhancement, Chang E E, Goldberg J L, Ophthalmology. 2012 May; 119(5):979-86). However, these interventions not always halt progression of the glaucoma and loss of vision among patients.

Thus, there is a need in the art for compositions that are useful and effective in treating conditions of optical neuropathy, resulting from various reasons. The art does not provide any teaching that isolated fractions of mastic gum can be used for treating optical neuropathy conditions.

SUMMARY OF THE INVENTION

The present invention provides compositions having optical nerve neuro-regenerative properties and methods of using same for treating optic neuropathy conditions, such as, optical nerve ischemic condition, Glaucoma, and the like. More specifically, compositions comprising isolated fractions extracted from mastic gum are disclosed to be able to treat related conditions, such as those resulting from ischemia and/or trauma to the optic nerve.

In some embodiments, the present invention is based in part on the unexpected discovery that isolated fractions of mastic gum exhibit such enhanced optical-nerve regenerative biological activity. The present invention is further based on the unexpected discovery that even in the absence of (or having undetectable levels of) polymeric-myrcene within the isolated fractions, such fractions exhibit the enhanced beneficial activity on the optical nerve and on optical neuropathy conditions.

Extracts of mastic gum are known to comprise polymeric forms of the monoterpene compound known as myrcene. It is thus further disclosed herein that isolated fraction of mastic gum which does not include detectable levels of polymeric myrcene may be employed as an active ingredient in pharmaceutical compositions for treating optic neuropathy related disorders, such as, traumatic neuropathy, ischemic optic neuropathy, glaucoma, and the like.

According to some embodiments, there is provided the use of a composition comprising isolated fractions of mastic gum and a pharmaceutically acceptable carrier, for treating an optic neuropathy condition. In some embodiments, there is provided a method of treating an optic neuropathy condition, the method comprising administering a composition comprising isolated fractions of mastic gum and a pharmaceutically acceptable carrier, to a subject in need thereof.

According to further embodiments, there is provided a use of an isolated fraction of mastic gum, for the preparation of a medicament for treating optic neuropathy.

According to another aspect, there is provided an isolated fraction of mastic gum, for use in treating optic neuropathy.

According some embodiments, there is provided a pharmaceutical composition comprising an isolated fraction of mastic gum and a pharmaceutically acceptable carrier, for use in treating optic neuropathy.

In various embodiments, the composition may be administered by parenteral route. According to some embodiments the route of administration is via parenteral injection. In various embodiments, the step of administering is carried out by a parenteral route selected from the group consisting of intravenous (i.v.), intramuscular, subcutaneous (sc), intradermal, intraperitoneal, intraarterial, intracerebral, intracerebroventricular, intraosseus, intraocular, intravitreal, and intrathecal.

In some embodiments, the optic neuropathy condition comprises any condition in which the optic nerve is damaged. In some embodiments, the optic neuropathy condition may be selected from such conditions as, but not limited to: traumatic neuropathy (that may result from any type of trauma to the optic nerve); ischemic neuropathy (such as, for example, Non Arteritic Ischemic neuropathy (NAION), Anterior ischemic optic neuropathy (AION), Posterior ischemic optic neuropathy); Radiation optic neuropathy (RON)), Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy and the like; or combinations thereof. Each possibility is a separate embodiment.

In some embodiments, the optic neuropathy condition is NAION. In some embodiments, the optic neuropathy condition is glaucoma.

In some embodiments, the optic neuropathy condition is resulting from or is associated with damage to the optical nerve as a result of deposition of lipoproteinaceous substances in the optic nerve.

In some embodiments, the optic neuropathy condition is resulting from or associated with damage to the optical nerve as a result of deposition of lipoproteinaceous substances in the optic nerve, wherein the deposition of lipoproteinaceous substances is the result of a storage disease.

In some embodiments, the optic neuropathy condition is resulting from or associated with damage to the optical nerve as a result of deposition of lipoproteinaceous substances in the optic nerve, wherein the deposition of lipoproteinaceous substances is the result of a storage disease, and wherein the lipoproteinaceous substance is lipofuscin. In some embodiments, the deposition of lipoproteinaceous substances is in the sub retinal layers between the Bruch membrane and the RPE layer.

In some embodiments, the isolated fraction of mastic gum is characterized in that it is soluble in at least one polar organic solvent and in at least one non-polar organic solvent. In a particular embodiment, the isolated fraction of mastic gum is further characterized in that it is substantially devoid of compounds which are soluble in said polar organic solvent but insoluble in said non-polar organic solvent.

In some embodiments, the isolated fraction of mastic gum is characterized in that it is soluble in both at least one polar organic solvent and at least one non-polar organic solvent, and is substantially devoid of compounds which are soluble in said polar organic solvent but insoluble in said non-polar organic solvent.

According to some embodiments, the isolated fraction of mastic gum is obtained by a process comprising the step of treating mastic gum with at least one polar organic solvent and isolating a fraction soluble in said polar organic solvent. In a particular embodiment, the isolated fraction of mastic gum is obtained by a process comprising the step of treating mastic gum with at least one non-polar organic solvent and isolating a fraction soluble in said non-polar organic solvent.

In some exemplary embodiments, the isolated fraction of mastic gum is obtained by a process comprising the steps of:
(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent, (e) isolating a fraction soluble in said nonpolar organic solvent; and
(f) optionally removing said nonpolar organic solvent;
wherein steps (d) to (f) may precede steps (a) to (c).

In some embodiments, the process for obtaining the isolated fraction of mastic gum further comprises size fractionation of the soluble fraction obtained following step (c) or step (f). In a particular embodiment, the size fractionating comprises size exclusion chromatography. In a particular embodiment, steps (c) or (f) comprise removing the solvent by a means selected from the group consisting of rotary evaporation, application of high vacuum and a combination thereof. In a particular embodiment, steps (a) to (c) are carried out prior to steps (d) to (f). In a particular embodiment, steps (d) to (f) are carried out prior to steps (a) to (c). In a particular embodiment, the polar organic solvent comprises ethanol and the non-polar organic solvent comprises hexane. In a particular embodiment, steps (a) to (c) and steps (d) to (f) are each independently carried out for a number of cycles.

In some embodiments, polar organic solvents suitable for obtaining extracts useful in the methods of the invention include such polar solvents as, but not limited to alcohols, ethers, esters, amides, aldehydes, ketones, nitriles and combinations thereof. Particular examples of polar organic solvents are methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof. Each possibility is a separate embodiment.

In some embodiments, non-polar solvents suitable for use in the preparation methods of the isolated fraction may include such solvents as, but not limited to: acyclic or cyclic, saturated or unsaturated aliphatic hydrocarbons and aromatic hydrocarbons, for example, C5-C10 alkanes, C5-C10 cycloalkanes, C6-C14 aromatic hydrocarbons, and combinations thereof. Each of the foregoing may be optionally substituted by one or more halogens, for example, C7-C14 perfluoroalkanes Particular examples of non-polar organic solvents are pentanes, hexanes, heptanes, octanes, nonanes, decanes, cyclopentane, cyclohexane, cycloheptane, benzene, toluene, xylene, and isomers and mixtures thereof. Each possibility is a separate embodiment.

In some embodiments, the mastic gum is obtained from a species of *Pistacia* selected from the group consisting of *P. lentiscus, P. atlantica, P. palestina, P. saportae, P. terebinthus, P. vera* and *P. integerrima*. Each possibility is a separate embodiment.

In some embodiments, the composition may include from about 0.01 to about 25% (w/w) of an isolated fraction of mastic gum, based on the total weight of the composition. In some embodiments, the composition comprises from about 0.01 to about 12% (w/w) of an isolated fraction of mastic gum, based on the total weight of the composition. In some embodiments the composition comprises from about 1% to about 10% of an isolated fraction of mastic gum, based on the total weight of the composition. In some embodiments the composition comprises from about 1% to about 5% of an isolated fraction of mastic gum, based on the total weight of the composition. In some embodiments the composition comprises from about 1% to about 3% of an isolated fraction of mastic gum, based on the total weight of the composition. In some embodiments the composition contains about 10% of an isolated fraction of mastic gum, based on the total weight of the composition. In some embodiments the composition contains about 5% of an isolated fraction of mastic gum, based on the total weight of the composition. In some embodiments, the composition comprises about 0.01%; 0.05%; 0.1%; 0.5%; 1%; 2%; 3%; 4%; 6%; 7%; 8%; 9%; 11%; 12%; 13%; 14%; 15%; 16%; 17%; 18%; or 19% (w/w) of an isolated fraction of mastic gum.

In some embodiments, the isolated fraction of mastic gum does not include detectable amounts of polymeric myrcene. In some embodiments, the isolated fraction of mastic gum is substantially devoid of polymeric myrcene. In some embodiments, the isolated fraction of mastic gum includes a non-detectable amount of polymeric myrcene.

In particular embodiments, the composition comprises less than about 10% (w/w), and more preferably, less than about 5% (w/w), of terpene compounds which are soluble in a polar organic solvent and insoluble in a non-polar organic solvent. In particular embodiments, the composition is substantially devoid of terpene compounds which are soluble in a polar organic solvent and insoluble in a non-polar organic solvent. In some embodiments, the composition comprises less than about 10% (w/w). In some embodiments, the composition comprises less than about 5% (w/w), of monomeric terpene compounds. In a particular embodiment, the composition is substantially devoid of myrcene monomers.

As referred to herein, terpene compounds include monomeric and oligomeric forms of terpene compounds, including those variously classified as monoterpenes, diterpenes, and sequiterpenes. In a particular embodiment, the composition comprises less than about 10% (w/w), and more preferably, less than about 5% (w/w), of a monoterpene compound selected from the group consisting of: β-myrcene, α-myrcene, cis-α-ocimene, dihydromyrcene, limonene, α-pinene, β-pinene and combinations thereof.

In some embodiments, the isolated fraction of polymeric myrcene is derived from a plant and the composition is substantially devoid of terpene compounds which are soluble in at least one polar organic solvent and insoluble in at least one non-polar organic solvent.

In a particular embodiment, the pharmaceutically acceptable carrier comprises a hydrophobic carrier. In some embodiments, the pharmaceutically acceptable hydrophobic carrier comprises at least one oil. In a particular embodiment, the oil is selected from the group consisting of a mineral oil, a vegetable oil and combinations thereof. In a particular embodiment, the vegetable oil is selected from the group consisting of almond oil, canola oil, coconut oil, corn oil, cottonseed oil, grape seed oil, olive oil peanut oil, saffron oil, sesame oil, soybean oil, and combinations thereof. In a particular embodiment, the mineral oil is light mineral oil. In a particular embodiment, the oil is cottonseed oil. In a particular embodiment, the hydrophobic carrier comprises at least one wax. In a particular embodiment, the hydrophobic carrier comprises a combination of at least one oil and at least one wax.

In some embodiments, the composition is in a form selected from the group consisting of a capsule, a tablet, a liposome, a suppository, a suspension, an ointment, a cream, a lotion, a solution, an emulsion, a film, a cement, a powder, a glue, an aerosol and a spray.

In some embodiments, the composition is a pharmaceutical composition.

In some embodiments, the subject is a human. In some embodiments the subject is a non-human mammal.

According to some embodiments, there is provided a use of a composition comprising an isolated fraction of mastic gum and a pharmaceutically acceptable carrier, for treating an optic neuropathy condition, wherein said fraction of mastic gum is characterized in that it is soluble in at least one polar organic solvent and in at least one non-polar organic solvent, and wherein said fraction is substantially devoid of compounds which are soluble in said polar organic solvent but insoluble in said non-polar organic solvent.

In some embodiments, the optic neuropathy condition may be selected from traumatic neuropathy, ischemic neuropathy; Radiation optic neuropathy (RON), Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy and combinations thereof. In some embodiments, the ischemic neuropathy optic may be selected from: Non arteritic Ischemic neuropathy (NAION), Anterior ischemic optic neuropathy (AION) and Posterior ischemic optic neuropathy. Each possibility is a separate embodiment.

In some embodiments, the optic neuropathy condition may result from or caused by a storage disease. In some embodiments, the storage disease may cause deposition of lipoprotenaceous substances in the optical nerve. In some embodiments, the lipoproteinaceous substance deposited in the optic nerve is lipofucsin. In some embodiments, the storage disease may cause deposition of mineral substances. In some embodiments, the mineral substances deposited in the optic nerve contain calcium and/or iron.

In some embodiments, the composition may be administered by parenteral route. In some embodiments, the parenteral route may be selected from the group consisting of intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseus. intraocular and intrathecal. Each possibility is a separate embodiment. In some embodiments, the composition is administered by subcutaneous administration.

In some embodiments, the isolated fraction of mastic gum may be substantially devoid of polymeric myrcene.

In some embodiments, the at least one polar organic solvent may be selected from the group consisting of an alcohol, an ether, an ester, an amide, an aldehyde, a ketone, a nitrile, and combinations thereof. In some embodiments, the polar organic solvent may be selected from the group consisting of methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof. Each possibility is a separate embodiment.

In some embodiments, the at least one non-polar organic solvent may be selected from the group consisting of acyclic or cyclic, saturated or unsaturated aliphatic hydrocarbons and aromatic hydrocarbons, each of which is optionally substituted by one or more halogens, and combinations thereof. In some embodiments, the non-polar organic solvent may be selected from the group consisting of C5-C10 alkanes, C5-C10 cycloalkanes, C6-C14 aromatic hydrocarbons and C7-C14 perfluoroalkanes, and combinations thereof. In some embodiments, the non-polar organic solvent may be selected from the group consisting of pentanes, hexanes, heptanes, octanes, nonanes, decanes, cyclopentane, cyclohexane, cycloheptane, benzene, toluene, xylene, and isomers and mixtures thereof. Each possibility is a separate embodiment.

In some embodiments, the isolated fraction may be obtained by a process including the steps of:

(a) treating mastic gum with a polar organic solvent;

(b) isolating a fraction soluble in said polar organic solvent;

(c) optionally removing said polar organic solvent;

(d) treating the soluble fraction obtained in step (b) or (c) with a non-polar organic solvent, (e) isolating a fraction soluble in said non-polar organic solvent; and (f) optionally removing said non-polar organic solvent;

wherein steps (d) to (f) may precede steps (a) to (c).

In some embodiments, the process may further include the step of size fractionating the fraction obtained in step (c) or step (f). In some embodiments, either or both of steps (c) and (f) comprise removing the solvent by a means selected from the group consisting of rotary evaporation, application of high vacuum and a combination thereof. In some embodiments, the process may further include repeating steps (a) to (c) and/or steps (d) to (f) for a multiplicity of cycles.

In some exemplary embodiments, the polar organic solvent may be ethanol and the non-polar organic solvent may be hexane.

In some embodiments, the mastic gum is obtained from a species of *Pistacia* selected from the group consisting of *P. lentiscus, P. atlantica, P. palestina, P. saportae, P. terebinthus, P. vera* and *P. integerrima*.

In some embodiments, the carrier is a hydrophobic carrier, selected from the group consisting of at least one oil, at least one wax and combinations thereof. In some embodiments, the at least one oil is selected from the group consisting of almond oil, canola oil, coconut oil, corn oil, cottonseed oil, grape seed oil, olive oil peanut oil, saffron oil, sesame oil, soybean oil and combinations thereof.

According to some embodiments, there is provided a method of treating optical neuropathy condition, the method comprising administering to a subject in need thereof a therapeutically effective amount of an isolated fraction of mastic gum, wherein the isolated fraction of mastic gum is characterized in that it is soluble in at least one polar organic solvent and in at least one non-polar organic solvent, and wherein the isolated fraction of mastic gum is substantially devoid of compounds which are soluble in said polar organic solvent but insoluble in said non-polar organic solvent and a pharmaceutically acceptable carrier, thereby treating the optical neuropathy condition.

Other objects, features and advantages of the present invention will become clear from the following description and drawings.

DETAILED DESCRIPTION OF THE INVENTION

Figure 1:
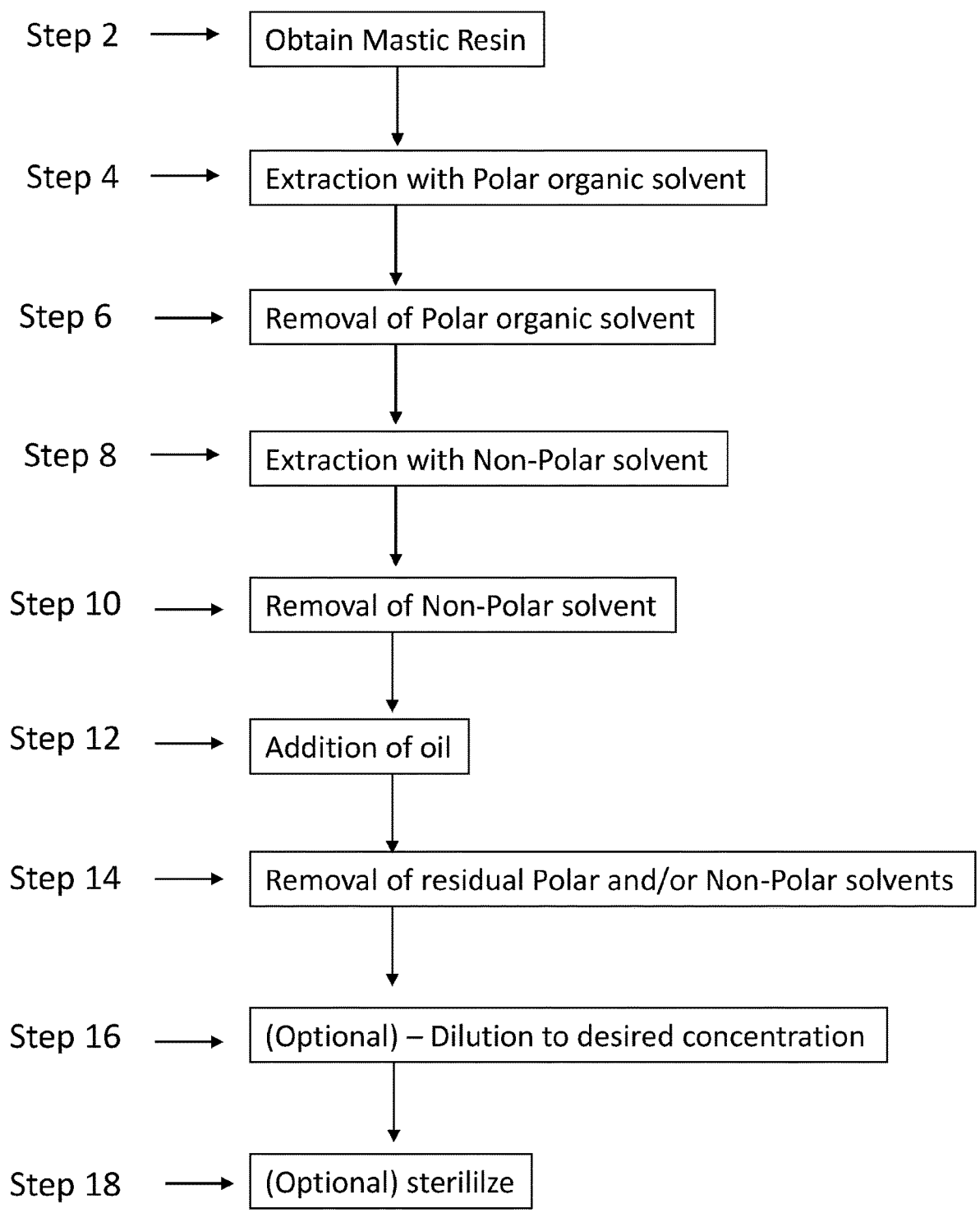
FIG. 1—A schematic illustration of steps in a process of obtaining an isolated fraction of mastic gum, according to some embodiments.

According to some embodiments, there are provided compositions comprising isolated fractions extracted from mastic gum, and uses thereof for treating optical neuropathy.

It is herein disclosed for the first time that the disclosed isolated fraction of mastic gum as described herein, may be employed as an active ingredient in a pharmaceutical composition for treating optical neuropathy, (resulting from various consequences), which are severe conditions that may lead to loss of vision in afflicted subjects.

Definitions

As used herein, the terms "mastic", "mastic resin", "gum mastic" and "mastic gum", are used interchangeably to refer to a tree resin (also known as an oleoresin) obtained as an exudate from any tree classified in the family Anacardiaceae. Trees in the genus *Pistacia*, most notably *Pistacia lentiscus* L., and in particular the cultivar *P. lentiscus* L. cv. Chia (cultivated on the Greek island of Chios), are known for their high yield of mastic. Other varieties include *P. lentiscus* L. var. *emarginate* Engl., and *P. lentiscus* L. var. *latifolia* Coss. Additional species of *Pistacia* include for example, *P. atlantica*, *P. palestina*, *P. saportae*, *P. terebinthus*, *P. vera* and *P. integerrima*.

As used herein, the term "polymer" refers to a compound or a mixture of compounds, comprising repeating subunits (also referred to as monomers) of the same chemical structure, wherein the monomers are in covalent connection. An example of a monomer from which a polymer may be formed is a terpene, for example a monoterpene such as myrcene. Polymers may have various degrees of polymerization and thus encompass polymeric forms of various chain length. Polymers include homopolymers and heteropolymers (also known as copolymers), and may have various isomeric and diastereoisomeric configurations.

As used herein, the terms "polymeric myrcene" and "polymyrcene" interchangeably refer to a polymer formed from myrcene monomers. Polymeric myrcene encompasses polymeric forms having various degrees of polymerization and preferably myrcene polymers having a degree of polymerization of at least 6. The invention encompasses without limitation, polymeric β-myrcene (poly-β-myrcene), polymeric α-myrcene (poly-α-myrcene), homopolymers thereof, heteropolymers (also known as copolymers) comprising myrcene monomers in direct or indirect covalent connection with heterologous monomers, trans- and cis-isomers thereof, D- and L-enantiomers thereof, or combinations thereof. Polymeric myrcene may be obtained in isolated form from a plant source, in particular from mastic, or may be the product of a chemical synthesis reaction.

As used herein, the term "an isolated fraction of mastic gum" refers to a fraction obtained following extraction of gum mastic in at least one polar or non-polar organic solvent, or combinations thereof. The isolated fraction of the invention is generally soluble in either or both of polar and non-polar organic solvents.

As used herein, "terpene compounds" refers to isoprene-containing hydrocarbons and related oxygen-containing compounds such as alcohols, aldehydes or ketones (terpenoids). The isoprene unit ($CH_2=C(CH_3)-CH=CH_2$) is the basic building block of such compounds. Terpene hydrocarbons in general, have the molecular formula $(C_5H_8)_n$, and include monoterpenes, sesquiterpenes, diterpenes, which respectively have 2, 3, 4 isoprene units. Terpenes may be further classified as acyclic or cyclic. Examples of monoterpenes include myrcene, limonene and pinene, which are respectively examples of acyclic, monocyclic and bicyclic monoterpenes. Examples of sesquiterpenes include nerolidol and farnesol. Examples of diterpenes include cafestol and phytol.

As used herein, "substantially devoid" means that a preparation or pharmaceutical composition according to the invention that generally contains less than 3% of the stated substance, preferable less than 1% and most preferably less than 0.5%.

As used herein, "detectable levels" refers to an amount of more than about 3% of the stated substance, more than 1% of the stated substance, preferably not more than 0.5 and most preferably not more than 0.1%. In accordance, the term "non-detectable levels" refers to an amount of not more than 3% of the stated substance, not more than 1% of the stated substance, preferably not more than 0.5 and most preferably not more than 0.1%.

As used herein, "therapeutically effective amount" refers to that amount of a pharmaceutical ingredient which substantially induces, promotes or results in a desired therapeutic effect.

As used herein, "pharmaceutically acceptable carrier" refers to a diluent or vehicle which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject.

As used herein, "pharmaceutically acceptable hydrophobic carrier" refers to a hydrophobic non-polar diluent or vehicle in which the isolated fraction of mastic gum and/or polymeric myrcene is dissolved or suspended.

As used herein, the terms "optic neuropathy" and "optic atrophy" may interchangeably be used. The terms refer to damage to the optic nerve due to any cause. The terms further encompass any condition or disorder resulting from or related to optic neuropathy, such as, ischemic optic neuropathy (including non Arteritic Ischemic neuropathy (NAION), Anterior ischemic optic neuropathy (AION), Posterior ischemic optic neuropathy); Radiation optic neuropathy (RON)); Traumatic optic neuropathy, Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy, damage resulting from storage disease, and the like; or combinations thereof. Each possibility is a separate embodiment.

As used herein, the term "storage disease" refers to any type of metabolic disorder that lead to excessive accumulation of substances such as lipids, proteins, lipoproteins, carbohydrates and others, of normal or abnormal nature. Of particular importance is the accumulation of lipofuscin associated with pathological damage to the optic nerve.

Numerical values stated herein are to be understood as the stated value +/−10%.

The term "about" is directed to include the stated value +/−10% of the stated value.

According to some embodiments, the present invention provides for isolated fractions of mastic gum and uses thereof for the treatment of optic neuropathy. The isolated fraction of mastic gum may be obtained from a plant source, in particular mastic gum, or it may be the product of a chemical synthesis. Plant species from which an isolated fraction of mastic gum may be obtained are of the genus *Pistacia* and can be selected from the species *P. lentiscus, P. atlantica, P. palestina, P. saportae, P. terebinthus, P. vera* and *P. integerrima*.

According to some embodiments, methods used for obtaining isolated fractions of mastic gum include, by way of a general description, such steps as: collected plant material, for example mastic gum, is combined in a suitable vessel with a suitable solvent, usually a polar solvent. Suitable polar solvents include for example, alcohols, ethers, esters, amides, aldehydes, ketones, nitriles and combinations thereof. Particular examples of polar organic solvents are methanol, ethanol, propanol, isopropanol, 1-butanol, 2-butanol, sec-butanol, t-butanol, 1-pentanol, 2-pentanol, 3-pentanol, neopentanol, 3-methyl-1-butanol, 2-methyl-1-butanol, 3-methyl-2-butanol, 2-methyl-2-butanol, ethyleneglycol, ethyleneglycol monomethyl ether, diethyl ether, methylethyl ether, ethylpropyl ether, methylpropyl ether, 1,2-dimethoxyethane, tetrahydrofuran, dihydrofuran, furan, pyran, dihydropyran, tetrahydropyran, methyl acetate, ethyl acetate, propyl acetate, acetaldehyde, methylformate, ethylformate, ethyl propionate, methyl propionate, dichloromethane, chloroform, dimethylformamide, acetamide, dimethylacetamide, N-methylpyrrolidone, acetone, ethylmethyl ketone, diethyl ketone, acetonitrile, propionitrile, and combinations thereof.

According to some embodiments, the mastic gum and the solvent may be combined such that the solvent is in large excess, for example 10:1 or 20:1. The mixture may be periodically or continuously agitated over a period ranging from a few minutes to a number of hours. The solvent may be decanted without any treatment, or optionally the mixture may be first subjected to low speed centrifugation, for example at 100 to 2000 rpm. The insoluble material is recovered from the extract and a fresh aliquot of solvent is added to the insoluble material, such that the extraction and dissolution process is repeated for a number of cycles, in order to obtain as much as possible of the polar solvent soluble compounds. After the final dissolution step, the extracts containing polar solvent soluble material are combined and the polar solvent is evaporated (for example by using a rotary evaporation as is known in the art), so as to yield polar solvent soluble material, which may be referred to as a crude, or "first step" extract.

According to some embodiments, the first step extract material may combined with a non-polar organic solvent and extracted by shaking over a period of 1-24 hours. Suitable non-polar solvents include, for example, acyclic or cyclic, saturated or unsaturated aliphatic hydrocarbons and aromatic hydrocarbons, for example, C5-C10 alkanes, C5-C10 cycloalkanes, C6-C14 aromatic hydrocarbons, and combinations thereof. Each of the foregoing may be optionally substituted by one or more halogens, for example, C7-C14 perfluoroalkanes Particular examples of non-polar organic solvents are pentanes, hexanes, heptanes, octanes, nonanes, decanes, cyclopentane, cyclohexane, cycloheptane, benzene, toluene, xylene, and isomers and mixtures thereof.

According to some embodiments, material remaining insoluble or precipitating in the presence of the non-polar solvent may be removed and discarded. The non-polar solvent-soluble fraction may then be obtained by evaporating the non-polar solvent (for example by rotary evaporation). This fraction may be referred to as purified or "two step" extract, corresponding to an isolated fraction of mastic gum which is characterized by the fact that it is soluble in both a polar solvent and a non-polar solvent, while materials which are soluble in the polar solvent but insoluble in the non-polar solvent, have been removed. This feature distinguishes the isolated fractions of the invention over prior art extracts of mastic gum, the latter of which generally include a wide variety of compounds which are soluble only in polar solvents. According to the teachings of the present invention, such compounds interfere with the beneficial biological activities of the isolated fractions disclosed herein.

In some embodiments, the two step extract may be dried further, for example by high vacuum treatment (for example <0.01 mbar for up to several days) to remove residual solvent and other volatile material, weighed and combined with a suitable non-polar organic solvent or other carrier to effect its dissolution. The obtained fractions may be used directly, or further purified, characterized and/or fractionated using means known in the art.

Reference is now made to FIG. 1, which is a schematic illustration of steps in a process of obtaining an isolated fraction of mastic gum, according to some embodiments. As shown in FIG. 1, at step 2, Mastic gum resin is obtained. Next, at step 4, the resin is extracted with a polar organic solvent. The polar organic solvent (such as, of example, ethanol), is added to the resin and incubated (for example, in the dark) for a period of time, optionally with occasional shaking. The organic polar solvent (containing the extract) is transferred to a clean vessel. Fresh polar organic solvent is added to the remaining material, incubated for a period of time and transferred to the clean vessel (containing the first polar solvent fraction). Next, at step 6, the polar organic solvent is removed, for example, by evaporation. At step 8, non-polar solvent (such as, for example, Hexane), is added to the polar organic solvent extract, for a period of time, with occasional shaking, and incubated, preferably in the dark. The non-polar solvent (containing the extract) is transferred into a clean vessel. Fresh non-polar solvent is added to the remaining material, incubated for a period of time and transferred to the clean vessel (containing the first non-polar fraction). Next, at step 10, the non-polar solvent is removed (for example, by evaporation, in a rotary evaporator). Next, at step 12, oil (such as, for example, cotton seed oil) may be added to the extract. The amount of oil added may be determined based on the yield of the process. In some embodiments, the oil may be added to provide for a 20% (w/w) formulation. In some embodiments, the oil may be added to provide for a 5% (w/w) formulation. At step 14, any residual polar and/or non-polar solvents are removed (for example, by evaporation). Optionally, at step 16, the formulation may be diluted to a desired concentration in percentage (w/w) (for example 5% (w/w)). The dilution may be preformed, for example, by addition of required amount of oil. At optional step 18, the formulation may be further filtered and sterilized, for example, by sterile filtration using a 0.2 micron filter. The sterile formulation may be further filled in suitable vials/ampules and labeled.

In some embodiments, the isolated fractions of the invention may be obtained by a process comprising the steps of:
(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent,
(e) isolating a fraction soluble in said nonpolar organic solvent; and
(f) optionally removing said nonpolar organic solvent; wherein steps (d) to (f) may precede steps (a) to (c).

The process may further include size fractionating the soluble fraction obtained following step (c) or step (f), for example by size exclusion chromatography, or any other method known in the art.

In some embodiments, the process may further include removing the solvent after either or both of steps (c) or (f). Solvent removal may be carried out by any means known in the art, for example rotary evaporation, application of high vacuum and a combination thereof. In particular embodiments, steps (a) to (c) are carried out prior to steps (d) to (f) or vice versa. In a particular embodiment, the polar organic solvent comprises ethanol and the non-polar organic solvent comprises hexane. Steps (a) to (c) and steps (d) to (f) may each be independently carried out for a number of cycles to optimize the extraction process and degree of purification of the product.

According to some embodiments, for preparation of a composition for therapeutic use, suitable carriers may be used, such as hydrophobic carriers including pharmaceutically acceptable oils, optionally in combination with waxes, as described herein.

In some embodiments, the compositions comprising the fractions isolated from mastic gum as herein described, should comprise less than about 20% (w/w) of monomeric, oligomeric terpene compounds which are soluble in the polar organic solvent and are substantially insoluble in the non-polar organic solvent, wherein the aforementioned solvents refer to those used in the preparation of the fraction. More preferably, the isolated fractions comprise less than about 5% (w/w) of such terpene compounds. Even more preferably, the isolated fractions are substantially devoid of such terpene compounds.

The molecular weight of the polymeric product may be expressed in a number of ways, for example, weight average molecular weight or number average molecular weight, as is known in the art. Molecular weight may be determined by any of a number of means, such as light scattering, multi angle laser light scattering (MALLS), small angle neutron scattering, X-ray scattering, sedimentation velocity, viscometry (Mark-Houwink equation), mass spectrometry (e.g. MALDI-TOF) and gel permeation chromatography.

The polymeric myrcene may exist as different geometric isomers, resulting from the arrangement of substituents around the carbon-carbon double bond. Such isomers are designated as the cis- or trans-configuration (also referred to respectively as the Z or E configuration), wherein cis-(or Z) represents substituents on the same side of the carbon-carbon double bond, and trans-(or E) represents substituents on opposite sides of the carbon-carbon double bond. The various geometric isomers and mixtures thereof are included within the scope of the invention.

In some embodiments, the isolated fraction of mastic gum as used herein is substantially devoid of polymeric myrcene. In some embodiments, the isolated fraction of mastic gum does not include any detectable levels of polymeric myrcene. In some embodiments, the isolated fraction of mastic gum has un-detectable levels of polymeric myrcene.

According to some embodiments, there is provided a composition for use in treating an optical neuropathy condition, the composition comprises a therapeutically effective amount of an isolated fraction of mastic gum, and a pharmaceutically acceptable carrier. In some embodiments, the carrier is hydrophobic.

In some embodiments, a suitable hydrophobic carrier may include at least one oil, such as, for example a mineral oil, a vegetable oil or combinations thereof.

According to some embodiments, the term "mineral oil" refers to a clear colorless nearly odorless and tasteless liquid obtained from the distillation of petroleum. It may also be referred to as white oil, white mineral oil, liquid petrolatum, liquid paraffin or white paraffin oil. In accordance with a particular embodiment of the invention, the mineral oil is light mineral oil, a commercially available product which may be obtained either as a NF (National Formulary) grade product or as a USP (US Pharmacopoeia) grade product. For use in the invention, the mineral oil is preferably free of aromatics and unsaturated compounds.

According to some embodiments, suitable vegetable oils include, but are not limited to almond oil, canola oil, coconut oil, corn oil, cottonseed oil, grape seed oil, olive oil peanut oil, saffron oil, sesame oil, soybean oil, or combinations thereof. Each possibility is a separate embodiment. In accordance with a particular embodiment of the invention, the vegetable oil is a commercially available product which may be obtained either as a NF (National Formulary) grade product or as a USP (US Pharmacopoeia) grade product. In some embodiments, the mineral oil is light mineral oil. In some exemplary embodiments, the vegetable oil is cottonseed oil. In some embodiments the vegetable oil is cottonseed oil of NF (National Formulary) grade or of USP (US Pharmacopoeia) grade and suitable for parenteral administrations. In some embodiments, the oils maybe stabilized In some embodiments, in order to prevent the degradation caused by, for example, oxidation, antioxidants/stabilizers may be included in the formulation and the antioxidants are used in an amount which produces the desired function provided that the amount does not affect the stability of the solution. Antioxidants include, but are not limited to free radical scavengers and reducing agents such as, acetyl cysteine, ascorbic acid, butylated hydroxytoluene, green tea extract, caffeic acid, cysteine, tocopherol, ubiquinone, and propyl gallate, preferably 2,6-di-tert-butyl-4-methyl phenol (also known as butylated hydroxytoluene or "BHT", CAS nr. [128-37-0]).

According to some embodiments, the pharmaceutically acceptable carrier may alternately or in addition comprise a suitable oil replacement. Oil replacements include alkanes having at least 10 carbon (e.g., isohexadecane), benzoate esters, aliphatic esters, noncomodogenic esters, volatile silicone compounds (e.g., cyclomethicone), and volatile silicone substitutes. Examples of benzoate esters include $C_{12}C_{15}$ alkyl benzoate, isostearyl benzoate, 2-ethyl hexyl benzoate, dipropylene glycol benzoate, octyldodecyl benzoate, stearyl benzoate, and behenyl benzoate. Examples of aliphatic esters include $C_{12}C_{15}$ alkyl octonoate and dioctyl maleate. Examples of noncomodogenic esters include isononyl isononanoate, isodecyl isononanoate, diisostearyl dimer dilinoleate, arachidyl propionate, and isotridecyl isononanoate. Examples of volatile silicone substitutes include isohexyl decanoate, octyl isononanoate, isononyl octanoate, and diethylene glycol dioctanoate.

In some embodiments, the hydrophobic carrier may further include at least one wax. Waxes include for example, beeswax; vegetable waxes, sugar cane waxes, mineral waxes, and synthetic waxes. Vegetable waxes include for example, carnauba, candelilla, ouricury and jojoba wax. Mineral waxes include for example, paraffin wax, lignite wax, microcrystalline waxes and ozokerites. Synthetic waxes include for example, polyethylene waxes.

In some embodiments, the pharmaceutical composition may be formulated in any of a number of forms, suitable for the administration route, such as for example, a capsule (including a softgel capsule), a tablet, a gel, a liposome, a suppository, a suspension, an ointment, a solution, an emulsion or microemulsion, a film, a cement, a powder, a glue, an aerosol, a spray and a gel.

In some embodiments, for preparing the pharmaceutical composition, the isolated fraction may be suitably formulated as inclusion complexes, nanoemulsions, microemulsions, powders and liposomes. In a particular embodiment, an inclusion complex comprises at least one cyclodextrin. In a particular embodiment, cyclodextrins comprise hydroxypropyl-β-cyclodextrin. In a particular embodiment, nanoemulsions comprise droplets having average particle size of less than 800 nm. In a particular embodiment, the droplets have average particle size of less than 500 nm. In a particular embodiment, the droplets have average particle size of less than 200 nm. In a particular embodiment, powders are spray dried powders. In a particular embodiment, liposomes comprise multilamellar vesicles. In a particular embodiment, a microemulsion comprises a non-ionic surfactant. Non-ionic surfactants include, without limitation, polyoxyl castor oils, polyoxyethylene sorbitan fatty acid esters (polysorbates), a poloxamer, a vitamin E derivative, polyoxyethylene alkyl ethers, polyoxyethylene sterates, saturated polyglycolyzed glycerides or combinations thereof.

According to some embodiments, various formulations of isolated fraction and preparation thereof are disclosed herein in Example 1. The pharmaceutical compositions of the invention may be administered by any means that achieve their intended purpose. In some embodiments, administration is by parenteral route. In some embodiments, administration is a parenteral, localized administration. In some embodiments, parenteral administration may be selected from, but not limited to: intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseus, intraocular, and intrathecal routes of administration.

According to some embodiments, the dosage administered is dependent upon the age, health, and weight of the subject, the use of concurrent treatment, if any, frequency of treatment, and the nature of the effect desired. The amount of the isolated fraction of the present invention in any unit dosage form comprises a therapeutically effective amount which may vary depending on the recipient subject, route and frequency of administration.

According to some embodiments, the amount of the isolated mastic gum fraction present in the pharmaceutical composition may conveniently be in the range from about 0.01% to about 25%, such as 0.01% to about 12%, on a weight per weight basis, based on the total weight of the composition. For example, for administration by injection, the percentage of isolated mastic gum fraction in the composition may be in the range from about 0.1% to about 10%, for example, 10%, 7.5%, 5%, 3%, 2.5% 1.5%, 1% and 0.5%.

In some embodiments, the pharmaceutical compositions of the invention may be manufactured in a manner which is itself known to one skilled in the art, for example, by means of conventional mixing, granulating, dissolving, extracting, or lyophilizing processes.

In some embodiments, formulations for parenteral administration may include suspensions and microparticle dispersions of the active compounds as appropriate. In some embodiments, oily injection suspensions may be administered. Suitable lipophilic solvents or vehicles include fatty oils, e.g., sesame oil, or synthetic fatty acid esters, e.g., ethyl oleate, triglycerides, polyethylene glycol-400, cremophor, or cyclodextrins. Injection suspensions may contain substances which increase the viscosity of the suspension include, e.g., sodium carboxymethyl cellulose, sorbitol, and/or dextran. Optionally, the suspension may also contain stabilizers.

In some embodiments, pharmaceutical compositions can also be prepared using liposomes comprising the active ingredient. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. In general, the preferred lipids are phospholipids and the phosphatidyl cholines (lecithins), both natural and synthetic. Methods to form liposomes are known in the art, as disclosed for example, in Prescott, Ed., Methods in Cell Biology, Volume XIV, Academic Press, New York, N.Y. (1976) and in U.S. Pat. No. 7,048,943.

In some embodiments, the pharmaceutical composition may comprise an oil-in-water emulsion or microemulsion in order to facilitate its formulation for parenteral use Such emulsions/microemulsions generally include lipids, surfactants, optionally humectants, and water. Suitable lipids include those generally known to be useful for creating oil-in-water emulsions/microemulsions, for example fatty acid glyceride esters. Suitable surfactants include those generally known to be useful for creating oil-in-water emulsions/microemulsions wherein lipids are used as the oil component in the emulsion. Non-ionic surfactants may be preferred, such as for example, ethoxylated castor oil, phospholipids, and block copolymers of ethylene oxide and propylene oxide. Suitable humectants, if used, include for example propylene glycol or polyethylene glycol.

According to some embodiments, the pharmaceutical composition may be formulated in the form of a gel, such as a hydrogel formed from a gel-forming polymer such as carrageenan, xanthan gum, gum karaya, gum acacia, locust bean gum, guar gum. A hydrogel may be combined with an oil-in-water emulsion comprising the active ingredient.

According to further embodiments, there are provided therapeutic uses and methods of treating optic neuropathy. The methods comprise administering to the subject a therapeutically effective amount of a composition comprising an isolated fraction of mastic gum, as described herein.

In some embodiments, the step of administering the compositions may comprise any acceptable route including parenteral route. Parenteral administration includes, for example, intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseus. intraocular and intrathecal routes of administration. Each possibility is a stearate embodiment.

In some embodiments, the composition may be administered subcutaneously on a twice weekly schedule with even intervals. In some embodiments, the composition may be administered subcutaneously on a schedule of every second day. In some embodiments, the composition may be administered subcutaneously on a schedule of once every seventh day (once weekly). In some embodiments, the composition may be administered subcutaneously once a day.

In some embodiments, the composition may be administered subcutaneously as a 5% (w/w) formulation of the isolated fraction of mastic gum in cottonseed oil. In some embodiments, the composition may be administered subcutaneously as a 5% (w/w) formulation of the isolated fraction of mastic gum in stabilized cottonseed oil. In some embodiments, the formulation may include 20 mg of the drug substance (isolated fraction).

In some embodiments, the composition may be administered subcutaneously as a 5% (w/w) formulation of the isolated fraction of mastic gum in BHT-stabilized cottonseed oil. In some embodiments, the composition may be administered subcutaneously as a 5% (w/w) formulation of the isolated fraction of mastic gum in cottonseed oil, twice weekly schedule with even intervals. In some embodiments, the composition may be administered subcutaneously as a 5% (w/w) formulation of the isolated fraction of mastic gum in cottonseed oil, on a once a week schedule with even intervals (every seventh day). In some embodiments, the composition may be administered subcutaneously as a 5% (w/w) formulation of the isolated fraction of mastic gum in cottonseed oil, on a once daily schedule with even intervals.

In some embodiments, the composition may be administered subcutaneously in a dose of 0.4 milliliter (ML) of a 5% (w/w) formulation of the isolated fraction of mastic gum. In some embodiments, the composition may be administered subcutaneously in a dose of 0.2 milliliter (ML) of a 5% (w/w) formulation of the isolated fraction of mastic gum. In some embodiments, the composition may be administered subcutaneously in a dose of 0.8 milliliter (ML) of a 5% (w/w) formulation of the isolated fraction of mastic gum. In some embodiments, the composition may be administered subcutaneously in a dose of 0.4 milliliter (ML) as a 5% (w/w) formulation of the isolated fraction of mastic gum in cottonseed oil, twice weekly with even intervals. In some embodiments, the composition may be administered subcutaneously in a dose of 0.2 milliliter (ML) as a 5% (w/w) formulation of the isolated fraction of mastic gum in cottonseed oil, twice weekly with even intervals. In some embodiments, the composition may be administered subcutaneously in a dose of 0.8 milliliter (ML) as a 5% (w/w) formulation of the isolated fraction of mastic gum in cottonseed oil, twice weekly with even intervals.

In some embodiments, the dosage of the drug substance (isolated fraction of mastic gum) may be in the range of 5-200 mg in any suitable formulation. In some embodiments, the dosage of the drug substance (isolated fraction of mastic gum) may be in the range of 0.1 mg-200 mg in any suitable formulation. In some embodiments, the dosage of the drug substance (isolated fraction of mastic gum) may be in the range of 200 mg-600 mg in any suitable formulation. In some embodiments, the drug substance may be administered at a dosage of 20 mg of the drug substance (in a suitable formulation). In some embodiments, the drug substance may be administered at a dosage of 40 mg of the drug substance (in a suitable formulation). In some embodiments, the drug substance may be administered at a dosage of 50 mg of the drug substance (in a suitable formulation). In some embodiments, the drug substance may be administered at a dosage of 60 mg of the drug substance (in a suitable formulation). In some embodiments, the drug substance may be administered at a dosage of 80 mg of the drug substance (in a suitable formulation). In some embodiments, the drug substance may be administered at a dosage of 100 mg of the drug substance (in a suitable formulation).

In some embodiments, the composition may be administrated 1-7 times a week for 1-4 times a day. In some embodiments, the composition may be administered 4 times a week. In some embodiments, the composition may be administered 2 times a week. In some embodiments, the composition may be administered 1 time a week.

It is clear to a person skilled in the art that many variations of the above-indicated administration routes, schedules, doses and regimens can be envisaged and designed. It is to be understood that such variations in administration routes, schedules, doses and regimens are also within the scope of the current invention.

According to some embodiments, the methods disclosed herein for treating optic neuropathy are particularly advantageous for subjects afflicted with conditions resulting from or associated with damage to the optical nerve, such as, for example, glaucoma, Traumatic Neuropathy, Ischemic optic neuropathy, Glaucoma, Neuropathy caused by tumors, Neuropathy caused by infections, Mitochondrial optic neuropathies, Nutritional optic neuropathies, Radiation optic neuropathy, Toxic optic neuropathy, damage caused by deposition disease, and the like, or combinations thereof. Each possibility is a separate embodiment.

In some embodiments, the uses and methods disclosed herein for treating optic neuropathy are particularly advantageous for subjects afflicted with conditions resulting from or associated with damage to the optical nerve as a result of a deposition disease, such as, deposition of lipoproteinaceous substances in the optic nerve, deposition of lipofuscin.

In some embodiments, the uses and methods disclosed herein for treating optic neuropathy are particularly advantageous for subjects afflicted with conditions resulting from or associated with deposition of deposition of lipoproteinaceous substances in the optic nerve.

In some embodiments, the uses and methods disclosed herein for treating optic neuropathy are particularly advantageous for subjects afflicted with conditions resulting from or associated with damage to the optical nerve as a result of deposition of lipoproteinaceous substances in the optic nerve, wherein the deposition of lipoproteinaceous substances is the result of a storage disease.

In some embodiments, the uses and methods disclosed herein for treating optic neuropathy are particularly advantageous for subjects afflicted with conditions resulting from or associated with damage to the optical nerve as a result of deposition of lipoproteinaceous substances in the optic nerve, wherein the deposition of lipoproteinaceous substances is the result of a storage disease, and wherein the deposited lipoproteinaceous substance is lipofuscin.

In some embodiments, the uses and methods disclosed herein for treating optic neuropathy are particularly advantageous for subjects afflicted with conditions resulting from or associated with damage to the optical nerve as a result of deposition of mineral substances in the optic nerve, wherein the deposition of mineral substances is the result of a storage disease, and wherein the mineral substances deposited in the optic nerve contain calcium and/or iron.

In some embodiments, the compositions disclosed herein may be used to improve best-corrected visual acuity (BCVA) (i.e., best distance vision with eyeglasses or contact lenses) in subjects afflicted with optic neuropathy condition, such as, of example, NAION. In some embodiments, the BCVA may be improved by 10 or more ETDRS (Early Treatment Diabetic Retinopathy Study), after treatment with the compositions disclosed herein. The ETDRS charts are characterized by a proportional layout and a geometric progression of letter sizes be adopted as the "gold standard" for visual acuity measurement in population studies and clinical research.

In some embodiments, the uses and methods of treatment disclosed herein are suitable for application in humans and non-human mammals.

According to some embodiments, the methods of the invention may encompass use of an article of manufacture which incorporates the composition comprising isolated fraction of mastic gum, as described herein.

In some embodiments, the pharmaceutical composition may be in the form of a coating on the article of manufacture, or may be contained within a vessel which is integral to the article of manufacture.

In some embodiments, the pharmaceutical composition may be incorporated to a delivery device such as a needle, an injection device or a spray dispenser from which the composition is delivered to a body site requiring the therapy.

In some embodiments, articles of manufacture include, but are not limited to a needle, a microneedle, an injection device and a spray dispenser.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1 Preparation of Isolated Fractions of Mastic Gum (Substance Rph-DS-1) and Various Formulations Thereof Method 1—Preparation of Isolated Fraction of Mastic Gum (Referred to Herein as (Drug) Substance RPh-DS-1):

In a 10 L laboratory bottle (B1), mastic resin (250 g) was introduced, followed by addition of absolute ethanol (4 L). The mixture was allowed to stand at room temperature (preferably in the dark) for at least 12 hours. The mixture was shaken gently for 10-30 seconds in order to allow the ethanol to partly homogenize, without disturbing the non-dissolved resin particles on the bottom. The mixture was then allowed to stand for at least another 2 hours. The bottle containing the mixture was subsequently shaken for at least 15 minutes at 100-150 rpm on an orbital shaker, and was left to stand at least 15 minutes in order to allow larger particles to settle. The obtained ethanol solution (E1) was carefully decanted from insoluble material into a clean 10 L laboratory bottle (B2). To the insoluble material in bottle B1 was added fresh ethanol (2 L) and the mixture was shaken again for at least 15 minutes at 100-150 rpm on an orbital shaker. After standing at least 15 minutes, the second ethanol solution (E2) was carefully decanted into bottle B2 and thus combined with ethanol fraction E1. To the remainder in bottle B1 was added fresh ethanol (1 L), and the same sequence was repeated, yielding ethanol solution E3. Upon combining ethanol solution E3 with the already combined solutions E1 and E2, a total of 7 L of ethanol solution (E) was obtained in bottle B2.

The ethanol solution (E) in bottle B2 was divided in equal portions over five 3-liter evaporation flasks (F1-F5) and the ethanol was evaporated in vacuo using a rotary evaporator, while avoiding excessive foaming. Upon evaporation of the ethanol, 1.5 L of n-hexane was added to each of flasks F1-F5. The mixture was shaken for at least 1.5 hours on an orbital shaker at 120-150 rpm, and was then left to stand for at least 1.5 hours. The obtained n-hexane solutions from each flask were combined into a clean 15 L laboratory bottle (B3) by careful decantation. To the remainder in each of flasks F1-F5 additional 700 ml portion of fresh n-hexane was added, and the shaking and standing procedure was repeated. Upon combining the second n-hexane solutions into flask B3, about 11 L of hexane solution H was obtained. This solution was divided into five clean, pre-weighed 3 L evaporation flasks (F6-F10), and the n-hexane was evaporated in vacuo. The evaporation may be conducted in two steps, first adding 1.5 L hexane solution and evaporating most hexane, followed by adding the remaining 700 ml of hexane solution and completing the evaporation. Total yield of obtained drug substance in flasks F6-F10 after completion of evaporation ranged between 50-70% (125-175 gram), on most occasions between 55-65% (137.5-162.5 gram) of mastic resin starting material. The thus obtained isolated mastic gum fraction (referred to herein as (drug) substance RPh-DS-1)) had a white to off-white or slightly yellow color, and had a sticky foam/semi solid consistency at room temperature. The material would melt into a very viscous liquid/oily material above 35 to 40° C. When cooled below 15° C., the material becomes more solid.

Utilizing the same procedure with different solvent combinations, additional isolated fractions of mastic gum were prepared. These are summarized in Table 1 below.

TABLE 1

| Isolated fraction | Polar solvent used | Non-polar solvent used |
| --- | --- | --- |
| RPh-DS-2 | Ethanol | Heptane |
| RPh-DS-3 | Ethanol | Pentane |
| RPh-DS-4 | Ethanol | Cyclohexane |
| RPh-DS-5 | Ethanol | Cyclopentane |
| RPh-DS-6 | Methanol | Hexane |
| RPh-DS-7 | Methanol | Heptane |
| RPh-DS-8 | Methanol | Pentane |
| RPh-DS-9 | Methanol | Cyclohexane |
| RPh-DS-10 | Methanol | Cyclopentane |
| RPh-DS-11 | 2-propanol | Hexane |
| RPh-DS-12 | 2-propanol | Pentane |
| RPh-DS-13 | 2-propanol | Heptane |
| RPh-DS-14 | 2-propanol | Cyclohexane |

Method 2: Formulation of Isolated Mastic Gum Fraction (Drug Substance RPh-DS-1); Preparation of Formulation (Drug Product) RPh201-A (5% w/w), in BHT-Stabilized Cottonseed Oil.

To the isolated mastic gum fraction (drug substance RPh-DS-1) of above Method 1 in each flask (F6-F10) was added the amount of BHT-stabilized cottonseed oil (prepared as detailed in Example 2, Method 1, below), required to obtain a 5% (w/w) solution of drug substance in BHT-stabilized cottonseed oil. The flasks were shaken on an orbital shaker until clear and homogeneous solutions were formed. Each flask was subsequently subjected to further removal of residual ethanol and n-hexane in vacuo by rotary evaporation at 30° C. water bath temperature for at least 2 hours. Reaching a vacuum of 0.1 mbar or less was sometimes needed in order to efficiently remove residual solvents below 5000 ppm for ethanol and below 200 ppm for n-hexane. Residual levels of ethanol and n-hexane were measured by a gas-chromatographic procedure.

Upon vacuum treatment of 3-5 hours at a water bath temperature of 30° C., the levels of residual ethanol and n-hexane were found to be below respectively 5000 ppm and 200 ppm. The oil solutions were then combined into a clean, pre-weighed 5 L laboratory flask. The typically obtained amounts of formulation ranged from 2.65-3.25 Kg (2.8-3.4 Liters). The solution was subjected to sterile filtration and, after passing testing for sterility and endotoxins, was aseptically filled into desired vials or ampoules.

Method 3: Formulation of Isolated Mastic Gum Fraction (Drug Substance RPh-DS-1)—Preparation of Formulation (Drug Product) RPh201-B (10% w/w), BHT-Stabilized Cottonseed Oil.

The concentrated formulation (10% (w/w)) of the isolated fraction of mastic gum was prepared essentially using the same procedure as described above in Method 2 of Example 1, but using half the amount of BHT-stabilized cottonseed oil. This resulted in a 10% (w/w) formulation of isolated mastic gum fraction (drug substance) in BHT-stabilized cottonseed oil (RPh201-B). This concentrated formulation may be used as an intermediate step in the production of RPh201-A (5% w/w). The RPh201-A 5% (w/w) formulation may be subsequently obtained by dilution of the 10% (w/w) RPh201-B formulation with the required amount of BHT-stabilized cottonseed oil.

Method 4: Formulation of Isolated Mastic Gum Fraction (Drug Substance RPh-DS-1)—Preparation of Formulation (Drug Product) RPh201-C (20% w/w) in BHT-Stabilized Cottonseed Oil.

The concentrated formulation (10% (w/w)) of the isolated fraction of mastic gum was prepared essentially using the same procedure as described above in Method 2 of Example 1, but using an amount of BHT-stabilized cottonseed oil that resulted in a 20% (w/w) formulation of isolated mastic gum fraction (drug substance) in BHT-stabilized cottonseed oil. This 20% (w/w) formulation of RPh-DS-1 in BHT-stabilized cottonseed oil referred to herein as RPh201-C. This more concentrated RPH201-C formulation may be used as an intermediate step in the production of RPh201-A (5% w/w). The RPh201-A 5% (w/w) formulation is subsequently obtained by dilution of the 20% (w/w) RPh201-C formulation with the required amount of BHT-stabilized cottonseed oil.

Method 5: Formulation of Isolated Mastic Gum Fraction (Drug Substance RPh-DS-1)—Preparation of Formulations Having Varying Concentrations Formulations of isolated fraction of mastic gum (drug substance) including of 0.01%; 0.05%; 0.1%; 0.5%; 1%; 2%; 3%; 4%; 6%; 7%; 8%; 9%; 11%; 12%; 13%; 14%; 15%; 16%; 17%; 18%; 19% (w/w) were prepared similarly by dilution of with required amounts of BHT-stabilized cottonseed oil. Instead of dilution of more concentrated formulations, all the exemplified concentrations may also be obtained by direct formulation of the isolated mastic gum fraction (drug substance RPh-DS-1) with the appropriate amount of BHT-stabilized cottonseed oil.

Formulations of the same concentrations were also prepared using cottonseed oil that did not contain any BHT as stabilizer as well as using different types of oils, including: almond oil, canola oil, coconut oil, corn oil, cottonseed oil, grape seed oil, olive oil, peanut oil, saffron oil, sesame oil, soybean oil, or combinations thereof.

It is to be understood that formulations of any desired concentration up to saturated solutions may be prepared by the above approaches, or by similar approaches as obvious to those to be considered skilled in the art.

Example 2: Preparation of BHT Stabilized Cottonseed Oil

Method 1: Preparation of BHT-Stabilized Cottonseed Oil.

To 9.991 Kg NF-grade cottonseed oil (CRODA INC. "Super Refined Cottonseed NF NP-LQ-(MH); SR40367"), 9 grams of BHT (2,6-di-tert-Butyl-4-methylphenol; Pharmacopeia Eur. grade or US Pharmacopoeia grade, CAS [128-37-0]) was added in a suitable vessel, and the mixture was stirred or shaken under exclusion of light until a clear and homogeneous solution was obtained. Stirring/shaking times were typically around 15-30 hours. The obtained material was cottonseed oil stabilized with 900 ppm of BHT. This material was stored in dark conditions under nitrogen blanket until further use. Optionally, the material may be subjected to vacuum treatment using a rotary evaporator and vacuum of at least 0.1 mbar for 1 hour at 30° C. The obtained solution is used for the preparation of preparation of the isolated fractions formulations (drug products, Example 1, Methods 1-5), as well as a Placebo (see below).

Method 2: Preparation of Placebo.

The BHT-stabilized cottonseed oil solution as prepared above was subjected to sterile filtration, and aseptically filled in desired vials/ampoules after passing sterility and endotoxin testing, for use as a control/placebo treatment.

Example 3: Use of Isolated Fractions of Mastic Gum in the Treatment of Ischemic Optic Neuropathy (ION)

Formulation of isolated fraction of mastic gum are used in treating ischemic optic neuropathy in tested subjects. A double blind study for the treatment of ischemic optic neuropathy (ION) is conducted, using 5% formulation of mastic gum isolated fraction (formulation RPh-201A, above), or placebo treatment (BHT-stabilized cottonseed oil solution, above). The isolated fraction of mastic gum formulation is administered subcutaneously (s.c.) into the skinfold of the left or right upper arm, right or left thigh, or right or left side of the abdomen of subjects having different types of optic nerve neuropathies, including traumatic neuropathy and ischemic optic neuropathy (Non arteritic ischemic neuropathy (NAION)). The subjects are treated twice a week by s.c. injection of the formulation (0.4 ml of 50 mg/ml solution, containing 5% of the RPh-DS1 in 95% BHT-stabilized cottonseed oil) for a period of 13-26 consecutive weeks.

Baseline condition of the subjects is determined prior to initiation of treatment and follow up testing during and after treatment are further conducted, in order to evaluate the subject condition.

The parameters used to assess the effect of treatment are: changes in visual acuity and visual field, changes in visual evoked potential and changes in optical coherence tomography (OCT). Among others, the following parameters are measured/determined, before, during and after treatment: Visual acuity (VA) test performance with best correction, based on ETDRS, Visual field (VF) of the patients was measured using the 24-2 full-threshold program on the Humphrey Visual Field (HVF) 24-2 program. Visual Evoked Potential (VEP) also known as the visual evoked response (VER), was used to record electrophysiological signal generated by neurons in the brain in response to visual stimulation. A stimulus generator used to select the desired stimulus type are: Flash VEP, Pattern VEP and Multifocal VEP. High resolution OCT, was used to measure the retinal nerve fiber layer thickness (RNFLT) and Change in the affected quadrant, Macular volume, and the like.

In addition, measurements of variables such as: Vital signs (HR, BP, Body temperature), Clinical laboratory tests (such as hematology, clinical chemistry, urinalysis and cytokines expression) may further be performed on each subject, prior to, during and/or after treatments.

Tested subjects include male or female over 18 years of age, which were diagnosed with ischemic optic neuropathy unilateral or bilateral, resulting from Traumatic Neuropathy or Ischemic optic neuropathy—Non Arteritic Ischemic Neuropathy (NAION), for a maximum period of three years after the traumatic event, being at least 6 months without any treatment following the event and stable (i.e., having no improvement of visual field and/or visual acuity). In the case of bilateral optical nerve neuropathy, the latest event is considered. The subjects are further characterized as having a corrected visual acuity equal or worse than 6/60 or visual field of less than 15 degrees or both.

In some experiments, subjects afflicted with one of the following conditions may be excluded from the experiment: Glaucoma, Neuropathy caused by tumors, Neuropathy caused by infections, Mitochondrial optic neuropathies, Nutritional, Radiation, Toxic optic neuropathies, Retinal diabetic complications, Hereditary optic neuropathies, Subjects with complete SCOTOMA beyond three quarters, Clinical evidence for presence of infection, Subject is receiving, or has received within six months corticosteroids, immuno-suppressive drugs, cytotoxic agents, radiation therapy and chemotherapy, subject has a history of alcohol or drug abuse within the last two years, female subjects who are pregnant or nursing, or of childbearing potential and are not using adequate contraception, Clinically significant and/or uncontrolled condition or other significant medical disease, abnormal Laboratory tests results, clinically significant uncontrolled retinal disease (AMD), having known allergy to any component of the formulation.

Provided herein is analysis of interim data obtained from the study, which included 23 subjects. The analysis was performed after 10 of the 23 enrolled subjects completed all study visits.

The interim study analysis was performed to assess any changes in visual acuity (VA) and visual field (VF) observed following the S.C. administration of RPh201-A formulation, two times a week during an overall treatment period of at least 13 consecutive weeks with an option to extend the treatment phase to another 13 weeks (up to 26 weeks total) in the case of absence of drug related serious adverse events, and at the follow-up visit at 3 month after end of treatment in subjects with optic nerve neuropathy.

Upon confirmation of eligibility, subjects were randomly assigned in a 1.5:1 ratio to one of two treatment arms, either 20 mg RPh201-A in 400 μL vehicle (cottonseed oil) or vehicle alone. In total, 12 subjects treated with RPh201-A and 8 patients treated with placebo are evaluated at the end of the trial.

Initially, treatment was given for 13 consecutive weeks and was allowed to be extended for another 13 weeks, i.e. a total of 26 weeks (if desired by the patient and/or the treating physician). At the end of the treatment, all subjects were followed for an additional 13 weeks off treatment.

At the interim timeline a total of nine subjects (6 patient treated with RPh201-A and 3 placebo-treated) had completed all visits ("initial cohort"). Of the 9 subjects, 8 agreed to extend their treatment for an additional 13 weeks, i.e. from 13 weeks to 26 weeks. One subject declined to continue treatment beyond 13 weeks. All 9 subjects returned for their off-drug visit that took place 13 weeks after the last dose. The remaining 11 subjects in the trial are part of a later cohort.

Following the completion of the visits of the subjects in the initial cohort, an interim review of the safety evaluations was performed on the subjects in the initial cohort (#001-010, including one subject (#004) that withdrew after 12 weeks). All 10 subjects experienced at least one Adverse Event (AE), with a total of eighty-one AEs reported prior to the data cutoff date. The most common System Organ Classes for reported AEs were General Disorders and Administration Site Conditions (8 subjects) and Nervous System Disorders (5 subjects).

No deaths have been reported during the study. Four serious adverse events (SAEs) occurred in two subjects. Subject #001 (treated with RPh201-A) experienced concurrent SAEs of moderate vertigo, dizziness and a mild decrease in left eye visual acuity, all of which were assessed as unrelated. Subject #004 (treated with RPh201-A which withdrew from the study after visit 12) experienced an SAE of severe brucellosis, also assessed as unrelated. No AE resulted in discontinuation of study drug or withdrawal from the study.

No clinically significant changes in vital signs, including systolic blood pressure, diastolic blood pressure, and heart rate, or abnormal clinical laboratory assessments were observed during the study. There was no worsening in the unaffected fellow eyes in subjects receiving RPh201-A over the course of the study and/or the off-drug follow-up period.

An interim efficacy analysis was performed on the 10 subjects who completed all visits. Of the 10 subjects, 2 had previous NAION in both eyes, and both eyes of each subject were included in the analysis. Of the 2 bilateral-disease subjects, one was in the RPh201-A group and one was in the control group. Therefore, the efficacy analysis was of 11 eyes, 7 of which were in the RPh201A-treated group and 4 in the control group.

Efficacy analysis was performed on the following parameters: visual acuity, visual fields, and retinal nerve fiber layer thickness by optical coherence tomography (OCT). The results indicated that RPh201A treated subjects showed a trend towards improvement in visual acuity compared to placebo treated subjects, with most improving best-corrected visual acuity (BCVA) by 10 or more ETDRS (Early Treatment Diabetic Retinopathy Study) chart letters from baseline at 26 weeks. The ETDRS charts are characterized by a proportional layout and a geometric) progression of letter sizes be adopted as the "gold standard" for visual acuity measurement in population studies and clinical research.

Figure 2:
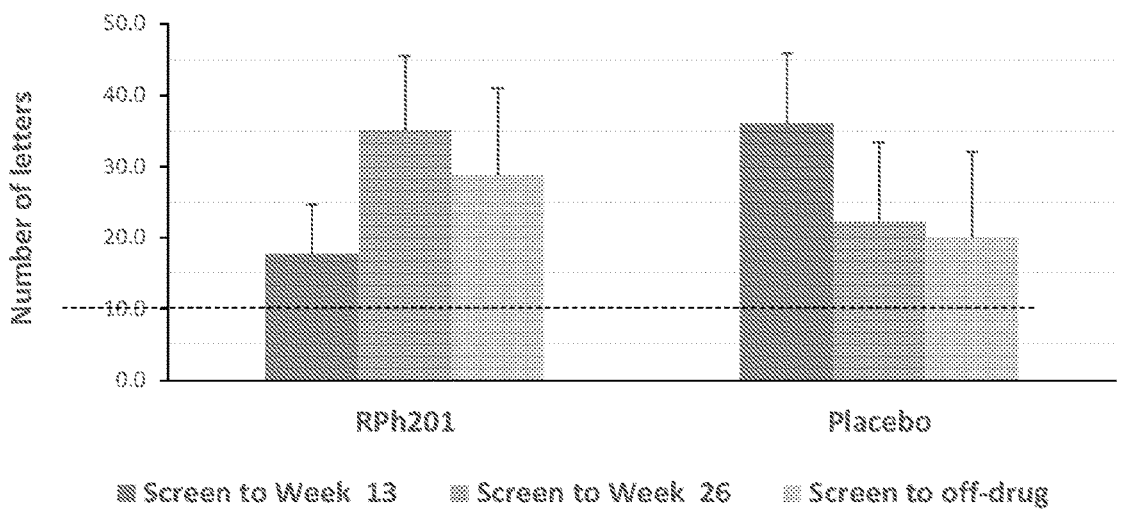
FIG. 2—A bar graph showing mean Increase from Baseline in ETDRS Letters Read at various time points (13 Weeks, 26 Weeks and Off-Drug Follow-Up Visit) in subjects treated with the isolated fraction of mastic gum ("RPH-201") or subjects treated with Placebo.

After 13 weeks of treatment, the RPh201 group showed less improvement in BCVA than the placebo group (mean±SEM: 17.7±7.0 vs. 36.0±9.9 letters improved from baseline, respectively; p=0.1563). However, after 26 weeks of treatment, the RPh201 group had greater improvement in BCVA from baseline than the placebo group (35.2±10.4 vs. 22.2±11.2 letters improved, respectively; p=0.3252). After the 13-week off-drug follow-up period, BCVA in both RPh201 and placebo groups declined slightly compared to baseline, with BCVA still being higher in RPh201 treated subjects compared to placebo (28.9±9.1 and 20.0±12.1 letters, respectively; (p=0.5498). The results are presented in FIG. 2, which shows the mean Increase from baseline in ETDRS letters read at 13 Weeks, 26 Weeks and off-drug follow-up visit, in treated ("RPH201") or non-treated ("Placebo") subjects.

Figure 3:
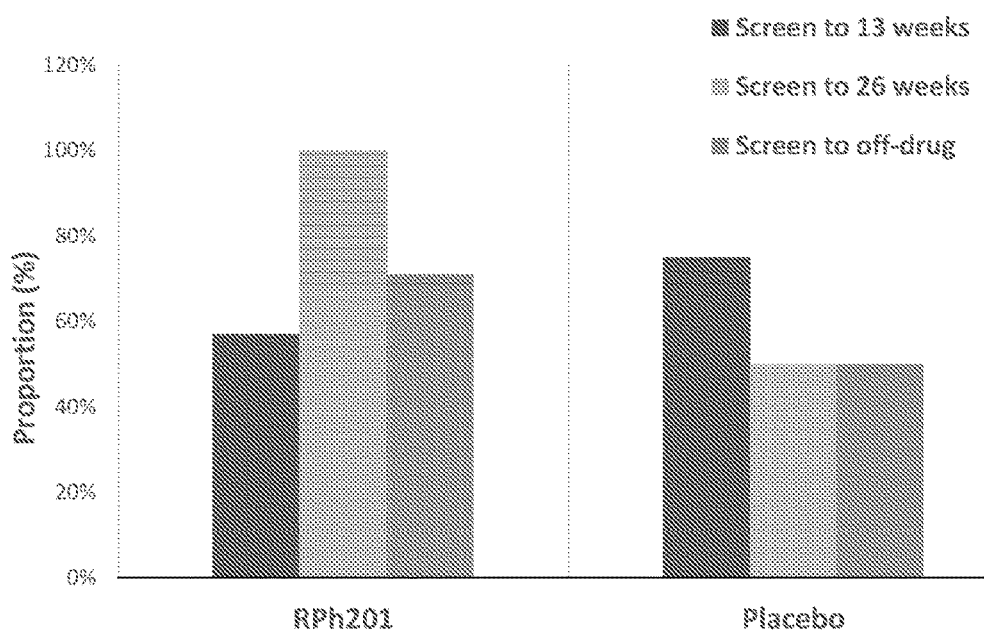
FIG. 3—A bar graph showing the proportion of subjects with increase of 10 or more letters as determined at various time points (13 Weeks, 26 Weeks and Off-Drug Follow-Up Visit) for subjects treated with the isolated fraction of mastic gum ("RPH-201") or Placebo treated subjects.

Comparisons of mean improvement in BCVA from baseline did not detect a significant difference between the treatment groups. However, after 26 weeks of treatment, 6 (100%) of the 6 eyes in the RPh201 group achieved an improvement of >10 letters (2 lines) of vision, compared to 2 (50%) of 4 eyes in the placebo group. At the 13 weeks off-drug follow-up, 5 (71%) of the 7 eyes in the RPh201 group showed improvement of >10 letters (2 lines) of vision, compared to 2 (50%) of 4 eyes in the placebo group. The results are presented in FIG. 3, which shows the proportion of subjects with increase of 10 or more letters in treated subjects ("RPH201") and non treated subjects ("Placebo")

Conclusion: The results presented show that s.c. administration of 20 mg of RPh201A twice weekly for 6 months was well tolerated and that administration site reactions were the most frequently reported treatment emergent adverse effects (TEAEs), with no TEAE related to vital sign measurements. Further, no worsening in the normal fellow eyes was observed in subjects receiving treatment over the course of the study and the off-drug follow-up period. Importantly, all RPh201-treated subjects improved BCVA by more than 10 ETDRS chart letters from baseline at 6 months, which indicates that the treatment is useful in improving visual function in patients with previous NAION.

Example 4: Use of Isolated Fractions of Mastic Gum in the Treatment of Glaucoma Using in-Vitro Models The aim of these experiments is to identify protection activity of RPh201 compositions (including, RPh201A, RPh201B and/or RPh201C) using direct cell treatment by RPh201 or by serum taken from rats pre-treated with RPh201, in mixed primary rat retinal ganglion cells undergoing apoptosis.

There is a wide variety of animal models of glaucoma including pigs, dogs, monkeys and rodents, most of these models involve optic nerve damage mediated through ocular hypertension. Other established models available to study glaucoma rely on RGC induced-death upon genetic mutations, mechanical trauma to the optic nerve, toxic insult to retinal neurons, or the induction of retinal ischemia (Rodent models of glaucoma. Johnson T V, Tomarev S I. Brain Res Bull. 2010 Feb. 15; 81(2-3):349-58). Such models allow to study the processes leading to RGC death and differentiate between the different types of initial insults. In addition, there is an accumulating data from in vitro systems that partially resemble the heterogeneous complex natural environment and provide a strong and useful tool for studying critical principles in the glaucoma mechanism. One of the main in vitro systems that is applicable to glaucoma research is RGC primary culture isolated from freshly isolated rodent retina (Y. Otori, Use of purified retinal ganglion cells for an in vitro model to study glaucoma, in: J. Tombran-Tink, C. J. Barnstable, M. B. Shields (Eds.), Ophthal-mology Research: Mechanisms of the Glaucomas, Humana Press, Totowa, N.J., 2008, pp. 601-607). It is considered a powerful system for assessing the RGCs susceptibility to glaucomatous damage induced by specific factors, such oxidative stress, mitochondrial dysfunction, and neurotoxicity. (Kawasaki et al. Investigative ophtalmology vis.sci.2002 jun; 43(6); 1835-42.)

Materials and Methods

Cell culture plates were purchased from Becton Dickson (Bedford, Mass.). Minimal Essential Medium (MEM) and Phosphate Buffered Saline (PBS) are from Mediatech (Manassas, Va.). Fetal Calf Serum is from Gemini Bio-Products (West Sacramento, Calif.). Calcein-AM and 1,1'-Dioctadecyl-3,3,3',3'-Tetramethylindocarbocyanine Perchlorate (DiI) is from are from Molecular Probes (Eugene, Oreg.). Poly-L-lysine, Staurosporine, N-methyl-D-aspartate (NMDA) and Glutamate are from Sigma Aldrich (St. Louis, Mo.). Papain, ovomucoid, and DNase I are from Worthington Biochemical (Lakewood, N.J.). Annexin V Alexa Fluor 488 is from ThermoFisher (Waltham, Mass.).

Animals—

Young adults; 8-9 weeks old at study initiation, are injected twice a week for two weeks with RPh201. 72 hours after the last injection, animals are anesthetized with isoflurane for blood sampling. Under terminal anesthesia, the animals are bled retro orbital for blood samples. Pregnant female Sprague Dawley are obtained from Envigo (Indianapolis, Ind.). Two to five days after birth, the pups are anesthetized by hypothermia and their retinal ganglion cells (RGCs) are labeled by an injection of DiI into the superior colliculus. Two to four days after labeling, the pups are sacrificed by decapitation and their eyes are removed and rinsed in Hank's Balanced Salt Solution (HBSS). Retinas are then removed and placed in a 12 units/mL papain and 0.005% DNAse solution in Earl's Balanced Salt Solution (EBSS) for dissociation.

Primary Retinal Ganglion Cell Isolation and Culture—

Culture methods were adapted from Worthington Biochemical Corporation. In the hour prior to primary RGC isolation, 96-well culture plates are coated with poly-L-lysine (10 µg/ml) for at least 30 minutes, followed by aspiration and rinse with HBSS.

The retinas in a papain and DNAse solution are incubated for 30 minutes at 37 degrees Celsius with constant agitation. Thereafter, the solution is triturated 50 times with a 10 mL serological pipette, further dissociating the cells. The solution is then centrifuged for five minutes at 300 g at room temperature.

Then, the supernatant is removed and the cell pellet is resuspended in a 0.005% DNase solution in EBSS. A discontinuous density gradient is prepared with ovomucoid albumin-inhibitor solution and the vial is centrifuged for a second time for six minutes at 70 g. The supernatant is removed and the cells are resuspeded in DMEM supplemented with 5% FCS. The resultant cell solution is filtered through a 40 µm cell strainer. Cells are plated at 2000 cells/mm2 and incubated for 24 hours at 37 degrees Celsius with 5% CO2.

Serum Preparation—

Whole blood samples are collected in serum separation tubes without EDTA and kept for 0.5 hour after blood collection, centrifuged for 5 minutes in 3000 rpm. Serum is collected using filtered pipette tips and immediately stored at −80° C.

Treatment—

To induce apoptosis, cells are treated with either 1 mM NDMA, or by serum deprivation at the time they are initially plated. At the same time, cells are treated with serum taken from RPh201-treated rats, vehicle-treated rats, RPh201 or vehicle. A 10 µM solution of staurosporine serve as a positive control for cell death.

Assessment of Primary RGC Viability—

Annexin V Alexa Fluor 488 stains the permeable membranes of cells that have undergone apoptosis and has excitation and emission wavelengths of 495/515 nm. 24 hours after initial plating, 5 µL of Annexin V is added to each well and the cells are counted by fluorescence microscopy ten minutes later.

Calcein AM stains only live cells and also has excitation and emission wavelengths of 495/515 nm. As a control for Annexin V Alexa Fluor 488, some cells are instead stained with Calcein AM. 24 hours after initial plating, media is removed from some cells and replaced with a solution of Calcein AM in 1×PBS. 30 minutes later, the Calcein solution is removed and replaced with 1×PBS and the cells are counted by fluorescence microscopy.

Fluorescence Microscopy—All RGCs are stained with DiI which has excitation and emission wavelengths of 549 and 565 nm. Cells that fluoresce both green and red are RGCs that have undergone apoptosis, while those that fluorescence only red are live RGCs. Number of living RGCs are reported as the percent of total DiI stained cells that are not also stained with Annexin V Alexa Fluor 488. As a control, some cells are stained with Calcein AM instead of Annexin, and in this case, percent viable RGCs are reported as the number of cells stained with both DiI and Calcein over the total number of cells stained with DiI.

Example 5: Use of Isolated Fractions of Mastic Gum in the Treatment of Glaucoma Using in-Vitro Models The aim of these experiments is to identify protection activity of RPh201 compositions (including, RPh201A, RPh201B and/or RPh201C) for neuroprotection activity in mixed primary rat retinal ganglion cells undergoing apoptosis.

Materials and Methods

Cell culture plates are from Becton Dickson (Bedford, Mass.). Minimal essential medium (MEM) and phosphate buffered saline (PBS) are from Mediatech (Manassas, Va.). Fetal Calf Serum is from Gemini Bio-Products (West Sacramento, Calif.). Calcein-AM and 1,1'-dioctadecyl-3,3,3',3'-tetramethylindocarbocyanine perchlorate (DiI) are from Molecular Probes (Eugene, Oreg.). Poly-L-lysine, staurosporine, N-methyl-D-aspartate (NMDA) and glutamate are from Sigma Aldrich (St. Louis, Mo.). Papain, ovomucoid, and DNase I are from Worthington Biochemical (Lakewood, N.J.). Annexin V Alexa Fluor 488 is from ThermoFisher (Waltham, Mass.).

Animals—

Pregnant female Sprague Dawley are obtained from Envigo (Indianapolis, Ind.). Two to five days after birth, the pups are anesthetized by hypothermia and their retinal ganglion cells (RGCs) are labeled by bilateral stereotactic injection of DiI into the superior colliculus. Two to four days after labeling, the pups are sacrificed by decapitation and their eyes are removed and rinsed in Hank's Balanced Salt Solution (HBSS). Retinas are then removed and placed in a 12 units/mL papain and 0.005% DNAse solution in Earl's Balanced Salt Solution (EBSS) for dissociation.

Primary Retinal Ganglion Cell Isolation and Culture—

Culture methods are adapted from Worthington Biochemical Corporation. In the hour prior to primary RGC isolation, 96-well culture plates are coated with poly-L-lysine (10 µg/ml) for at least 30 minutes, followed by aspiration and rinsing with HBSS. The retinas in a papain and DNAse solution are incubated for 30 minutes at 37 degrees Celsius with constant agitation. The solution is then triturated 50 times with a 10 mL serological pipette, further dissociating the cells. The solution is then centrifuged for five minutes at 300 g at room temperature. Then, the supernatant is removed and the cell pellet resuspended in a 0.005% DNase solution in EBSS. A discontinuous density gradient is prepared with ovomucoid albumin-inhibitor solution and the vial is centrifuged for a second time for six minutes at 70 g. The supernatant is removed and the cells are resuspeded in DMEM supplemented with 5% FCS. The resultant cell solution is filtered through 40 µm sterile plastic mesh to remove clumps. Cells are plated at 2000 cells/mm$^2$ and incubated for 24 hours at 37 degrees Celsius with 5% $CO_2$.

Treatment—

To induce apoptosis, cells are treated with serum deprivation at the time they are initially plated. At the same time, cells are treated with 1, 2.5, 5, and 10 µL of RPh201. A 10 µM solution of staurosporine serves as a positive control for cell death.

Assessment of Primary RGC Viability—

Annexin V Alexa Fluor 488-24 hours after initial plating, 5 µL of Annexin V labeled with Alexa Fluor 488 is added to each well and the cells are counted by fluorescence microscopy ten minutes later.

Calcein AM—

As a control for Annexin V Alexa Fluor 488, some cells are stained with calcein AM instead. 24 hours after initial plating, media is removed from some cells and replaced with a solution of calcein AM in 1×PBS. 30 minutes later, the calcein AM solution is removed and replaced with 1×PBS and the cells are counted by fluorescence microscopy. Fluorescence Microscopy—Annexin V Alexa Fluor 488 binds to the phosphatidylserine that becomes exposed in the membranes of cells that are undergoing apoptosis. It has excitation and emission wavelengths of 495/515 nm. Calcein AM is not fluorescent, but becomes fluorescent inside live cells when esterases cleave the ester bond with the acetoxymethyl (AM) ester. It therefore stains only live cells and also has excitation and emission wavelengths of 495/515 nm. The two reagents are not used in the same wells for this reason.

All RGCs are retrograde labeled with DiI, which has excitation and emission wavelengths of 549 and 565 nm. Cells that fluoresce both green (with annexin V) and red are RGCs that are undergoing apoptosis, while those that fluoresce only red are live RGCs. Numbers of living RGCs is reported as the percent of total DiI stained cells that are not also stained with Annexin V Alexa Fluor 488. As a control, some cells are stained with calcein AM instead of annexin V, and in this case, percent viable RGCs are reported as the number of cells stained with both DiI and calcein over the total number of cells stained with DiI. Assessment of Neuroprotective Activity—The calculation of amount of neuroprotective activity is based on how well the test article decreases the additional apoptosis induced by an injury paradigm. In other words, if the baseline apoptosis is 10%, the injury causes the apoptosis to become 60%, and the test article decreases the apoptosis to 35%, then the neuroprotective activity is 50%. If the test article decreases the apoptosis back to 10%, then the neuroprotective activity is 100%.

The formula for this calculation is:

$$\text{Neuroprotective efficacy} = \frac{(\text{Apoptosis}_{injury} - \text{Apoptosis}_{test})}{(\text{Apoptosis}_{injury} - \text{Apoptosis}_{baseline})}$$

Results and Conclusions

Figure 4:
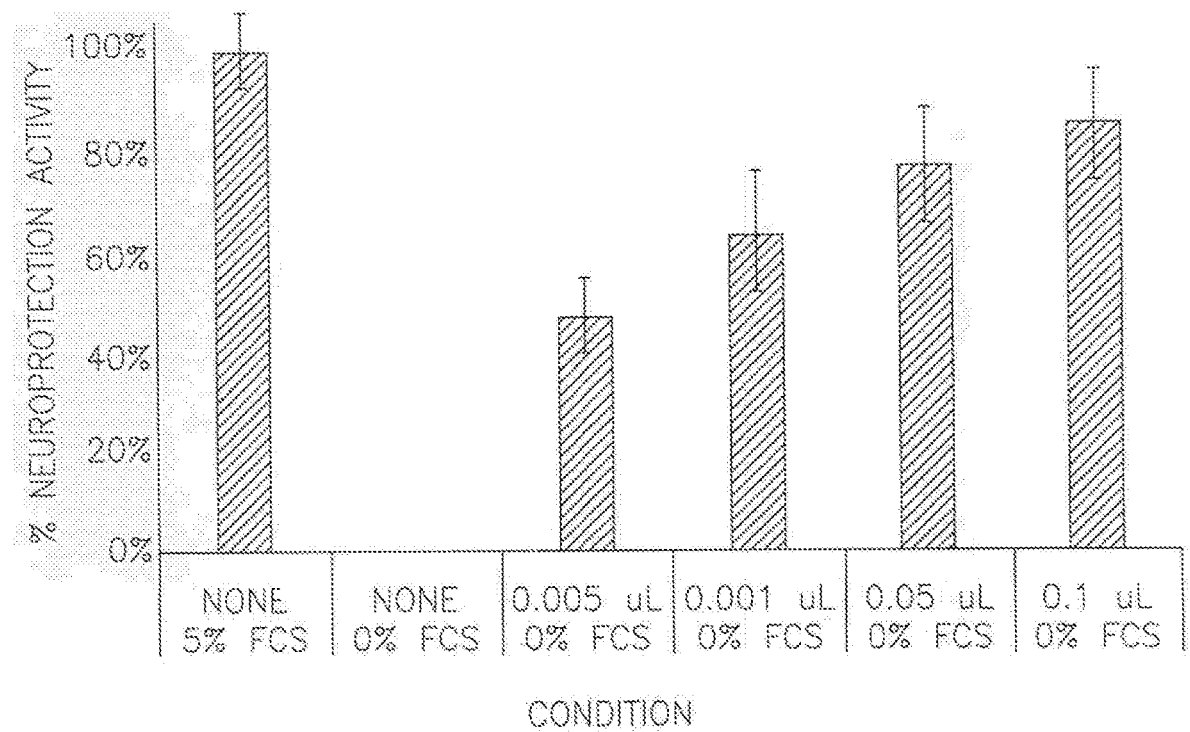
FIG. 4.—Bar graphs showing the neuroprotection activity induced by RPh201A on Primary Retinal Ganglion Cells. Primary Retinal Ganglion Cell were grown in normal conditions (5% serum) were no apoptosis was recorded. Under serum deprivation conditions, culture demonstrate a significant amount of apoptosis. This effect was rescue by adding RPh201 to the culture, by a dope dependent pattern.

As shown in the results presented in FIG. 4, serum deprivation caused a significant apoptosis ratio to the culture. The culture was rescued by RPh201A treatment in a dose-response, dose-dependent effect. Serum deprivation is commonly used model to mimic the loss of retrograde trophic support of RGCs during glaucoma, when the pressure and/or ischemia and/or stretch at the optic nerve head decreases axonal transport and causes axonal injury. Thus, the results presented demonstrate the neuroprotective effect of RPh201A in this well established in vitro glaucoma model.

Example 6: Use of Isolated Fractions of Mastic Gum in the Treatment of Glaucoma Using in-Vivo Model There are a variety of different types of glaucoma, all sharing the same pathophysiology of retinal ganglion cells (RGCs) loss. The common mechanism of the disease is the elevated intraocular pressure (TOP) that causes structural and functional damage to retinal ganglion cells (RGC). Therapeutic approaches that delay or halt RGCs loss have been recognized to be potentially beneficial to preserve vision in glaucoma. Thus, suitable animal models are those associated with optic nerve injury or inner retinal injury. Any injury to the optic nerve will consequently cause RGC death. Therefore, transecting the optic nerve either completely (Allcutt D, Berry M, Sievers J. A qualitative comparison of the reactions of retinal ganglion cell axons to optic nerve crush in neonatal and adult mice. Brain Res 1984; 318: 231-40; Allcutt D, Berry M, Sievers J. A quantitative comparison of the reactions of retinal ganglion cells to optic nerve crush in neonatal and adult mice. Brain Res 1984; 318: 219-30), or partially, can accomplish this. Same effect is achieved with chronic ischemia to the optic nerve head, induced by infusing endothelin-1 into the subarachnoid space around the nerve itself (Cioffi G A, Orgul S, Onda E, Bacon D R, Van Buskirk E M. An in vivo model of chronic optic nerve ischemia: the dose-dependent effects of endothelin-1 on the optic nerve microvasculature. Curr Eye Res 1995; 14: 1147-53; Orgul S, Cioffi G A, Bacon D R, Van Buskirk E M. An endothelin-1-induced model of chronic optic nerve ischemia in rhesus monkeys. J Glaucoma 1996; 5: 135-8.). In all mentioned models, induction of axonal injury result in RGC death.

In order to demonstrate a regenerative role of the RPh201A on the RGC after chronic damage, rat optic nerve axotomy model in which treatment of the animals started one month post surgery was used.

Methods:

Adult male Wistar rats (n=5), were deeply anaesthetized (xylazine 50 mg/kg and ketamine 35 mg/kg), and their right ON was exposed by lateral canthotomy. The conjunctiva was incised lateral to the eye globe at the border of the cornea. The optic nerve was exposed following isolation of the external and retractor bulbi muscles. Through a small opening in the meninges (50-100 μm), the nerve fibers were completely transected at a distance of 2-3 mm from the globe. A specially-designed glass dissector with a 50 μm tip and a smooth blunt edge assured that there would be no damage to the nerve vasculature and ON blood supply and there would be minimal damage to the meninges. The injury was unilateral in all animals.

Rats were divided into two experimental groups, each composed of 5 animals One group received a sub-dermal injection, containing a volume of 0.025 ml RPh201A, in the posterior neck area, the control group was injected with 0.025 ml of Vehicle.

The first injection was given to all the animals one month after the surgery. Subsequent injections administered twice a week for 3 months.

4 months after axotomy (3 months after treatment initiation), a fluorescent retrograde neurotracer (Di-Asp) was inserted into the axotomized optic nerve in order to stain surviving Retinal Ganglion Cells (RGC).

24 hours later, the operated rats were sacrificed in a $CO_2$ saturated chamber and the injured right eye was enucleated. The retinas were isolated, flattened on a slide and fixed with xylene based mounting medium.

Figure 5A:
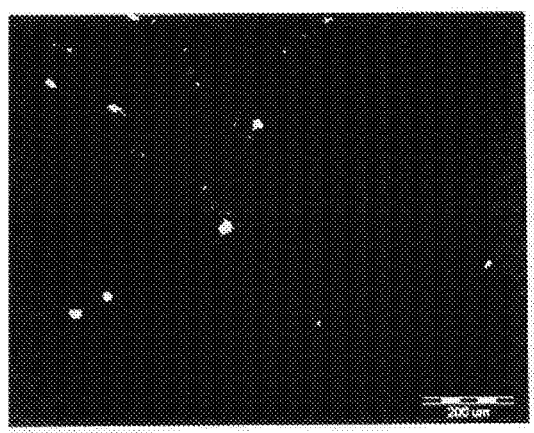
FIGS. 5A-B—pictograms of fluorescent microscopy images of retinas' RGC cells (indicative of RGC viability) obtained from rats that have undergone axotomy and one month later treated with either RPh201A (FIG. 5A) or vehicle (FIG. 5B), for a period of three months. FITC conjugated Di-Asp (retrograde neurotracer) was inserted into the optic nerve 24 hours prior animals were sacrificed. Retinas separated, flat-mounted on slides and visualized with fluorescent microscope. Magnification ×20.
Figure 5B:
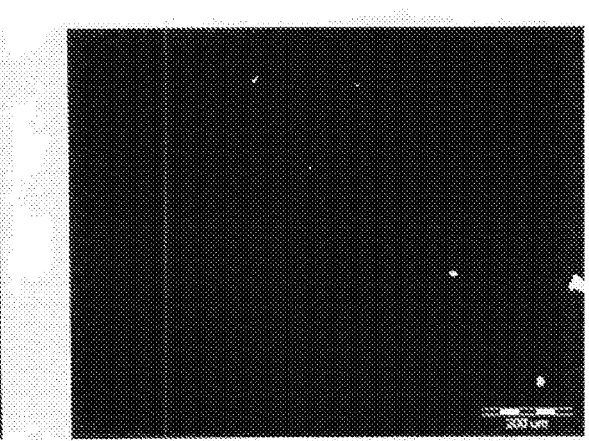

Whole-mount retinas were evaluated with a fluorescent microscope and dyed cells were counted manually. The results are presented in FIGS. 5A-B which show fluorescent microscope images of the retina analysis, exhibiting higher number of live RGC cells in obtained from RPh201A treated rats (FIG. 5A) as compared to the control (FIG. 5B).

Example 7: Use of Isolated Fractions of Mastic Gum in the Treatment of Glaucoma Using in-Vivo Model To demonstrate and evaluate the effect of RPh201 in treating Glaucoma, high intra ocular pressure (TOP) was performed in rat, to form a model which mimics the human glaucoma.

The use of micro beads injected in the anterior chamber of the eye is an established model to create high IOP in rats and other animals ("The micro beads occlusion model; A paradigm for induced ocular hypertension in rats and mice. IOVS, 2010 January; 51(1); 207-216"). The micro beads enter into the space of the anterior chamber angle and obliterates the exit of the aqueous from the eye, thereby increasing the intraocular pressure.

Materials and Methods

Young adult S.D. male rats, 8-9 weeks old at study initiation, are. The rats are acclimatized for one week. Two groups of 14 rats participate in the study. Group 1 is treated with RPh201A and group 2 serve as control and is treated with vehicle. All 28 rats are injected in the right eye in anterior chamber of latex micro beads measuring 15 micron in diameter. The volume of injection will be 8 μL of PBS containing a concentration of 5000 beads per 1 μL. The injection will be done using a Hamilton syringe of 10 μL volume and 32 G needle. The procedure will be done under general anesthesia using Xylasine 2% and KetamineHCl according to ARVO rules of Medical Care in Animals.

Group 1 is subcutaneously injected with RPh201A starting at the day of injection of beads. Group 2 (control) is subcutaneously injected with the vehicle (cottonseed oil). Administration of RPh201A or vehicle is performed twice a week.

The basal line IOP is measured before the injection. Starting three days following the injection, two IOP measurements are taken every week, using TONOPEN (Reichert Ltd, Germany) Local anesthetic eye drops Localin are used as well as short general anesthetics with Isofluran.

A difference of 8 mm Hg between the two eyes of each rat is considered as sufficient to be considered glaucoma. The study continues for 4 weeks starting the day of high IOP.

At the end of the study the animals are anesthetized and perfused transcardially with 0.1 M PBS followed by 4% paraformaldehyde in 0.1 M PBS (pH 7.4) for 10 min. The eyeballs, with retro-bulbar stumps of optic nerves, are removed and post-fixed in 4% paraformaldehyde for 3 hours. Optic nerve thus obtained is dissected and processed either for immunostaining or for toluidine blue staining (for counting axons).

Retinas are removed and processed for immunostaining as "whole mounted" retinas. Other eyeballs are embedded in paraffin, sectioned at a thickness of 5 mm, collected on slides, deparaffinized and hydrated, and processed for immunostaining to assess the number of RGCs.

In addition, in order to evaluate ultra-structural effects, several animals are sacrificed to obtained electron microscopy results.

The experiment is repeated using the RPh201B, RPh201C and other optional compositions as prepared according to the above-indicated examples.

Example 8: Use of Isolated Fractions of Mastic Gum in the Treatment of Glaucoma

Formulation of isolated fraction of mastic gum are used in treating glaucoma in tested subjects. A double bling study for the treatment of ischemic optic neuropathy (ION) is conducted, using 5% formulation of mastic gum isolated fraction (formulation RPH-201A, above), or placebo treatment (BHT-stabilized cottonseed oil solution, above). The isolated fraction of mastic gum formulation is administered subcutaneously (s.c.) to subjects suffering from varying degrees of glaucoma. The subjects are treated twice a week by s.c. injection of the RPH-201A formulation for a period of 13-26 consecutive weeks.

Baseline condition of the subjects is determined prior to initiation of treatment and follow up testing during and after treatment are further conducted, in order to evaluate the subject condition.

The parameters used to assess the effect of treatment are: changes in visual acuity and visual field, changes in visual evoked potential and changes in optical coherence tomography (OCT). Among others, the following parameters are measured/determined, before, during and after treatment: Visual acuity (VA) test performance with best correction, based on ETDRS, Visual field (VF) of the patients was measured using the 24-2 full-threshold program on the Humphrey Visual Field (HVF) 24-2 program. Visual Evoked Potential (VEP) also known as the visual evoked response (VER), was used to record electrophysiological signal generated by neurons in the brain in response to visual stimulation. A stimulus generator used to select the desired stimulus type are: Flash VEP, Pattern VEP and Multifocal VEP. High resolution OCT, was used to measure the retinal nerve fiber layer thickness (RNFLT) and Change in the affected quadrant, Macular volume.

In addition, measurements of variables such as: Vital signs (HR, BP, Body temperature), Clinical laboratory tests (such as hematology, clinical chemistry, urinalysis and cytokines expression) may further be performed on each subject, prior to, during and/or after treatments.

Tested subjects include male or female over 18 years of age, which were diagnosed with optic nerve damage as result of Glaucoma.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating optical neuropathy condition, the method comprising administering to a subject in need thereof a therapeutically effective amount of an isolated fraction of mastic gum and a pharmaceutically acceptable carrier, wherein the isolated fraction of mastic gum is characterized in that it is soluble in at least one polar organic solvent and in at least one non-polar organic solvent, and wherein the isolated fraction of mastic gum is substantially devoid of compounds which are soluble in said polar organic solvent but insoluble in said non-polar organic solvent, wherein the polar organic solvent is selected from the group consisting of methanol, ethanol, propanol, isopropanol, and combinations thereof, wherein the non-polar organic solvent is selected from the group consisting of C5-C10 alkanes, C5-C10 cycloalkanes and combinations thereof, and wherein the isolated fraction of mastic gum is substantially devoid of polymeric myrcene, thereby treating the optical neuropathy condition, wherein the optical neuropathy condition is non arteritic ischemic neuropathy (NAION).

2. The method of claim 1, wherein the composition is administered by parenteral route, selected from intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseus, intraocular and intrathecal.

3. The method of claim 1, wherein the carrier is a hydrophobic carrier, selected from the group consisting of at least one oil, at least one wax and combinations thereof.

4. The method of claim 3, wherein the at least one oil is selected from the group consisting of almond oil, canola oil, coconut oil, corn oil, cottonseed oil, grape seed oil, olive oil peanut oil, saffron oil, sesame oil, soybean oil and combinations thereof.

5. The method of claim 1, wherein the polar organic solvent is selected from the group consisting of methanol, ethanol and combinations thereof.

6. The method of claim 1, wherein the non-polar organic solvent is a C5-C10 alkane.

7. The method of claim 1, wherein the non-polar organic solvent is selected from the group consisting of pentanes, hexanes, heptanes, octanes, nonanes, decanes, cyclopentane, cyclohexane, cycloheptane and isomers and mixtures thereof.

8. The method of claim 1, wherein the polar organic solvent comprises ethanol and the non-polar organic solvent comprises hexane.

9. The method of claim 1, wherein the isolated fraction is obtained by a process comprising the steps of:
    (a) treating mastic gum with a polar organic solvent;
    (b) isolating a fraction soluble in said polar organic solvent;
    (c) optionally removing said polar organic solvent;
    (d) treating the soluble fraction obtained in step (b) or (c) with a non-polar organic solvent,
    (e) isolating a fraction soluble in said non-polar organic solvent; and
    (f) optionally removing said non-polar organic solvent;
    wherein steps (d) to (f) optionally precede steps (a) to (c).

10. The method of 9, wherein said process further comprises the step of size fractionating the fraction obtained in step (c) or step (f).

11. The method of claim 9, wherein either or both of steps (c) and (f) comprise removing the solvent by a means selected from the group consisting of rotary evaporation, application of high vacuum and a combination thereof.

12. The method of claim 9, wherein said process further comprises repeating steps (a) to (c) and/or steps (d) to (f) for a multiplicity of cycles.

13. The method of claim 1, wherein the mastic gum is obtained from a species of *Pistacia* selected from the group consisting of *P. lentiscus, P. atlantica, P. palestina, P. saportae, P. terebinthus, P. vera* and *P. integerrima.*

* * * * *